United States Patent
Igarashi et al.

(10) Patent No.: US 9,099,107 B1
(45) Date of Patent: Aug. 4, 2015

(54) STABILIZING LAYER FOR A SPIN TORQUE OSCILLATOR (STO)

(71) Applicant: HGST Netherlands B.V., Amsterdam (NL)

(72) Inventors: Masukazu Igarashi, Kawagoe (JP); Keiichi Nagasaka, Isehara (JP); Susumu Okamura, Fujisawa (JP); Yo Sato, Odawara (JP); Masashige Sato, Atsugi (JP); Masato Shimoto, Odawara (JP)

(73) Assignee: HGST Netherlands B.V., Amsterdam (NL)

( * ) Notice: Subject to any disclaimer, the term of this patent is extended or adjusted under 35 U.S.C. 154(b) by 0 days.

(21) Appl. No.: 14/604,635

(22) Filed: Jan. 23, 2015

(51) Int. Cl.
    *G11B 5/31* (2006.01)

(52) U.S. Cl.
    CPC .......................................... *G11B 5/31* (2013.01)

(58) Field of Classification Search
    CPC ..................... G11B 2005/0024; G11B 5/3146; G11B 5/1278; G11B 5/314; G11B 5/3133; G11B 2005/0005; G11B 2005/001; G11B 5/3163; G11B 5/3909; G11B 5/399; G11B 5/6005
    USPC ....................................................... 360/125.3
    See application file for complete search history.

(56) References Cited

U.S. PATENT DOCUMENTS

| | | | |
|---|---|---|---|
| 8,208,219 B2 | 6/2012 | Zhang et al. | |
| 8,274,811 B2 | 9/2012 | Zhang et al. | |
| 8,279,548 B2 | 10/2012 | Tsuchiya et al. | |
| 8,345,380 B2 | 1/2013 | Sato et al. | |
| 8,467,148 B2 | 6/2013 | Iwasaki et al. | |
| 8,472,135 B1 | 6/2013 | Kusukawa et al. | |
| 8,488,373 B2 | 7/2013 | Zhang et al. | |
| 8,582,240 B1 | 11/2013 | Chen et al. | |
| 8,625,235 B2 * | 1/2014 | Takano et al. | 360/125.15 |
| 8,687,319 B2 | 4/2014 | Igarashi et al. | |
| 8,824,103 B2 * | 9/2014 | Shiimoto et al. | 360/125.3 |
| 8,879,205 B2 * | 11/2014 | Shiimoto et al. | 360/125.3 |
| 8,970,996 B2 * | 3/2015 | Nagasaka et al. | 360/324 |
| 2008/0019040 A1 | 1/2008 | Zhu et al. | |
| 2012/0013408 A1 | 1/2012 | Cortadella et al. | |
| 2013/0070367 A1 | 3/2013 | Igarashi et al. | |
| 2013/0279039 A1 * | 10/2013 | Shiroishi | 360/48 |

FOREIGN PATENT DOCUMENTS

JP      5172004 B1    3/2013

OTHER PUBLICATIONS

Houssameddine et al., "Spin-torque oscillator using a perpendicular polarizer and a planar free layer," Nature Materials, vol. 6, Jun. 2007, pp. 447-453.
Satao et al., "Thin Spin-torque Oscillator With High AC-Field for High Density Microwave-Assisted Magnetic Recording," IEEE Transactions on Magnetics, vol. 49, No. 7, Jul. 2013, pp. 3632-3635.
Igarashi et al., U.S. Appl. No. 14/290,768, filed May 29, 2014.
Shiimoto et al., U.S. Appl. No. 14/179,358, filed Feb. 12, 2014.
Shiimoto et al., U.S. Appl. No. 14/555,484, filed Nov. 26, 2014.

* cited by examiner

*Primary Examiner* — Mark Blouin
(74) *Attorney, Agent, or Firm* — Zilka-Kotab, PC

(57) ABSTRACT

In one embodiment, a spin torque oscillator (STO) includes a reference layer having a magnetization that is capable of free in-plane rotation, a field generation layer (FGL) including at least one magnetic film having an easy magnetization plane effectively in a film plane, wherein a magnetization of the FGL is capable of in-plane rotation, and a stabilizing layer (STL) positioned on a side of the FGL opposite the reference layer, the STL including a magnetic film having an easy magnetization plane effectively in a film plane, wherein a magnetization of the STL is capable of in-plane rotation, wherein a product of a saturation magnetization of the STL multiplied by a thickness of the STL is less than half a product of a magnetization of the FGL multiplied by a thickness of the FGL.

20 Claims, 25 Drawing Sheets

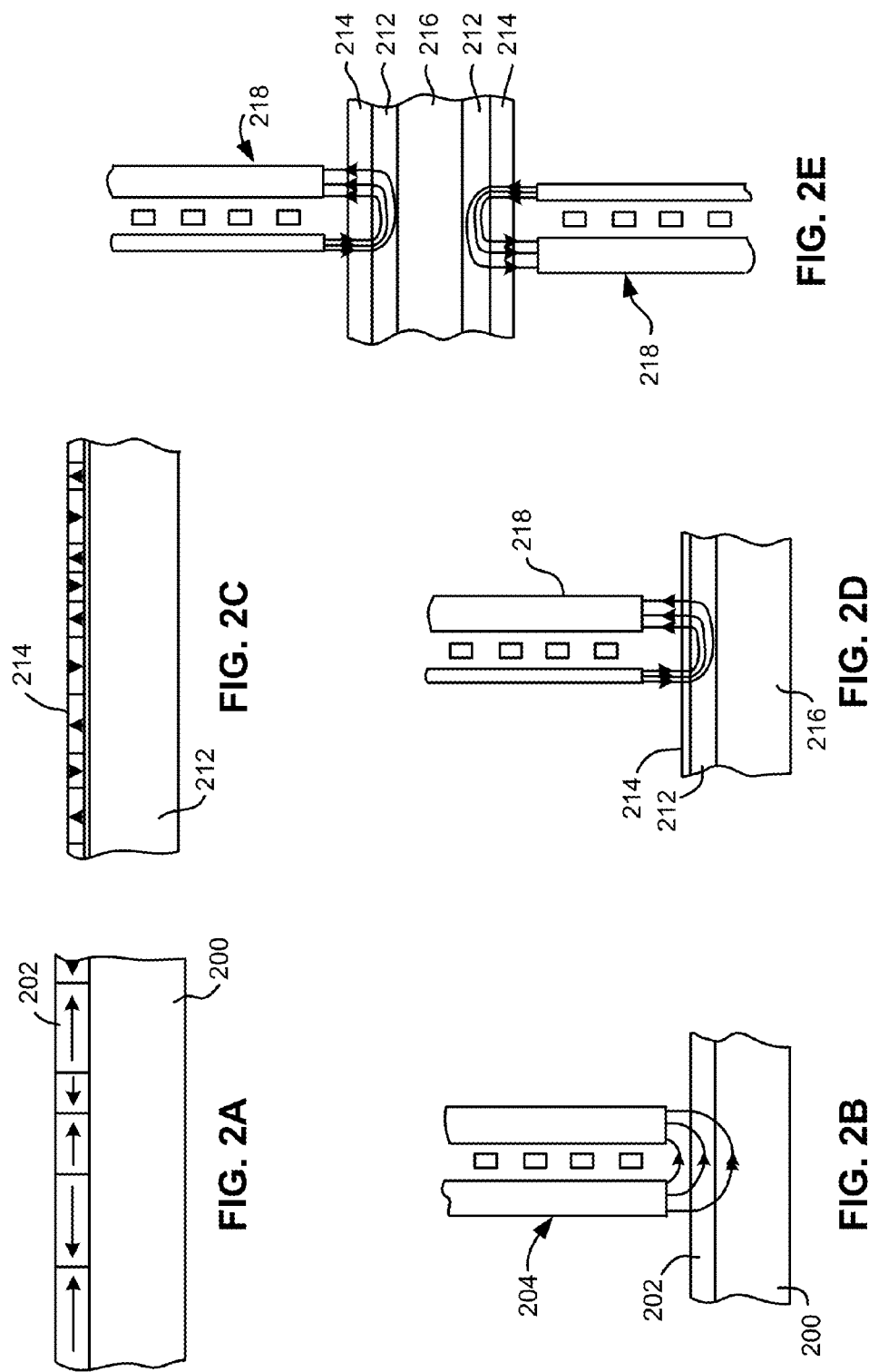

STABILIZING LAYER FOR A SPIN TORQUE OSCILLATOR (STO)

FIELD OF THE INVENTION

The present invention relates to magnetic recording, and more particularly, this invention relates to microwave-assisted magnetic recording (MAMR).

BACKGROUND

The heart of a computer is a magnetic hard disk drive (HDD) which typically includes a rotating magnetic disk, a slider that has read and write heads, a suspension arm above the rotating disk and an actuator arm that swings the suspension arm to place the read and/or write heads over selected tracks on the rotating disk. The suspension arm biases the slider into contact with the surface of the disk when the disk is not rotating but, when the disk rotates, air is swirled by the rotating disk adjacent an air bearing surface (ABS) of the slider causing the slider to ride on an air bearing a slight distance from the surface of the rotating disk. When the slider rides on the air bearing the write and read heads are employed for writing magnetic impressions to and reading magnetic signal fields from the rotating disk. The read and write heads are connected to processing circuitry that operates according to a computer program to implement the writing and reading functions.

The volume of information processing in the information age is increasing rapidly due to the increased capabilities of computers and increased network speeds and capacity. In order to efficiently receive, distribute, and extract such large volumes of information, storage devices are required that are capable of inputting/outputting large volumes of information at high speed. With magnetic disks, as the recording density is increased, a problem occurs where the recorded signal is progressively attenuated due to thermal fluctuation becoming increasingly acute. The cause of this problem is that the magnetic recording medium consists of magnetic material formed into an assembly of microcrystals, and the volume of these microcrystals is reduced. In order to achieve sufficient stability in regard to thermal fluctuation, it is useful to rely on the commonly-used thermal fluctuation index, $K\beta$, which equals $K_uV/kT$; where $K_u$ is magnetic anisotropy, V is grain volume, T is absolute temperature, and k is the Boltzmann's constant. $K\beta$ should be at least 70. If it is assumed that $K_u$ and T (material and environment) are fixed, it is seen that magnetization reversal due to thermal fluctuation will tend to increase as the volume, V, of the grains becomes smaller.

As recording densities are increased and the volume of the recording film occupied by one bit is decreased, thermal fluctuation cannot be neglected. If, in order to suppress this thermal fluctuation, $K_u$ is raised, the necessary magnetic field for magnetization reversal in magnetic recording exceeds the recording magnetic field that may be generated by the recording head, so recording becomes impossible.

SUMMARY

According to one embodiment, a device includes a main magnetic pole positioned at a media facing surface of the device, the main magnetic pole being configured to generate a writing magnetic field for storing information to magnetic recording media, and a spin torque oscillator (STO) positioned adjacent the main magnetic pole, the STO being configured to generate a high-frequency magnetic field to assist in storing the information to the magnetic recording media, wherein the STO includes: a field generation layer (FGL) including at least one magnetic film having an easy magnetization plane effectively in a film plane, wherein a magnetization of the FGL is capable of in-plane rotation, a reference layer having a magnetization that is capable of free in-plane rotation, and a stabilizing layer (STL) positioned on a side of the FGL opposite the reference layer, the STL including a magnetic film having an easy magnetization plane effectively in a film plane, wherein a magnetization of the STL is capable of in-plane rotation, and wherein a product of a saturation magnetization of the STL multiplied by a thickness of the STL is less than half a product of a magnetization of the FGL multiplied by a thickness of the FGL.

In another embodiment, a device includes a main magnetic pole positioned at a media facing surface of the device, and a STO positioned adjacent the main magnetic pole, wherein the STO includes: a FGL including at least one magnetic film having an easy magnetization plane effectively in a film plane, wherein a magnetization of the FGL is capable of in-plane rotation, a reference layer having a magnetization that is capable of free in-plane rotation, and a STL positioned on a side of the FGL opposite the reference layer, the STL including a magnetic film having an easy magnetization plane effectively in a film plane, wherein a magnetization of the STL is capable of in-plane rotation.

According to another embodiment, a device includes a main magnetic pole positioned at a media facing surface of the device, the main magnetic pole being configured to generate a writing magnetic field for storing information to magnetic recording media, and a STO positioned adjacent the main magnetic pole, the STO being configured to generate a high-frequency magnetic field to assist in storing the information to the magnetic recording media, wherein the STO includes: a reference layer including a Heusler alloy as a majority thereof having a magnetization that is capable of free in-plane rotation, a FGL including at least one magnetic film having an easy magnetization plane effectively in a film plane, wherein a magnetization of the FGL is capable of in-plane rotation, a first non-magnetic spin conducting layer positioned between the reference layer and the FGL, a STL positioned on a side of the FGL opposite the reference layer, the STL including a magnetic film having an easy magnetization plane effectively in a film plane, wherein a magnetization of the STL is capable of in-plane rotation, and a second non-magnetic spin conducting layer positioned between the STL and the FGL, wherein a product of a saturation magnetization of the STL multiplied by a thickness of the STL is less than half a product of a magnetization of the FGL multiplied by a thickness of the FGL, wherein a product of a saturation magnetization of the reference layer multiplied by a thickness of the reference layer is less than half a product of the magnetization of the FGL multiplied by the thickness of the FGL, and wherein a ratio of the thickness of the STL to the saturation magnetization of the STL is greater than about 2 nm/T.

Any of these embodiments may be implemented in a magnetic data storage system such as a disk drive system, which may include a magnetic head, a drive mechanism for passing a magnetic medium (e.g., hard disk) over the magnetic head, and a controller electrically coupled to the magnetic head.

Other aspects and advantages of the present invention will become apparent from the following detailed description, which, when taken in conjunction with the drawings, illustrate by way of example the principles of the invention.

BRIEF DESCRIPTION OF THE DRAWINGS

For a fuller understanding of the nature and advantages of the present invention, as well as the preferred mode of use, reference should be made to the following detailed description read in conjunction with the accompanying drawings.

FIG. 2A is a schematic representation in section of a recording medium utilizing a longitudinal recording format.

FIG. 2B is a schematic representation of a conventional magnetic recording head and recording medium combination for longitudinal recording as in FIG. 2A.

FIG. 2C is a magnetic recording medium utilizing a perpendicular recording format.

FIG. 2D is a schematic representation of a recording head and recording medium combination for perpendicular recording on one side.

FIG. 2E is a schematic representation of a recording apparatus adapted for recording separately on both sides of the medium.

DETAILED DESCRIPTION

Figure 1:
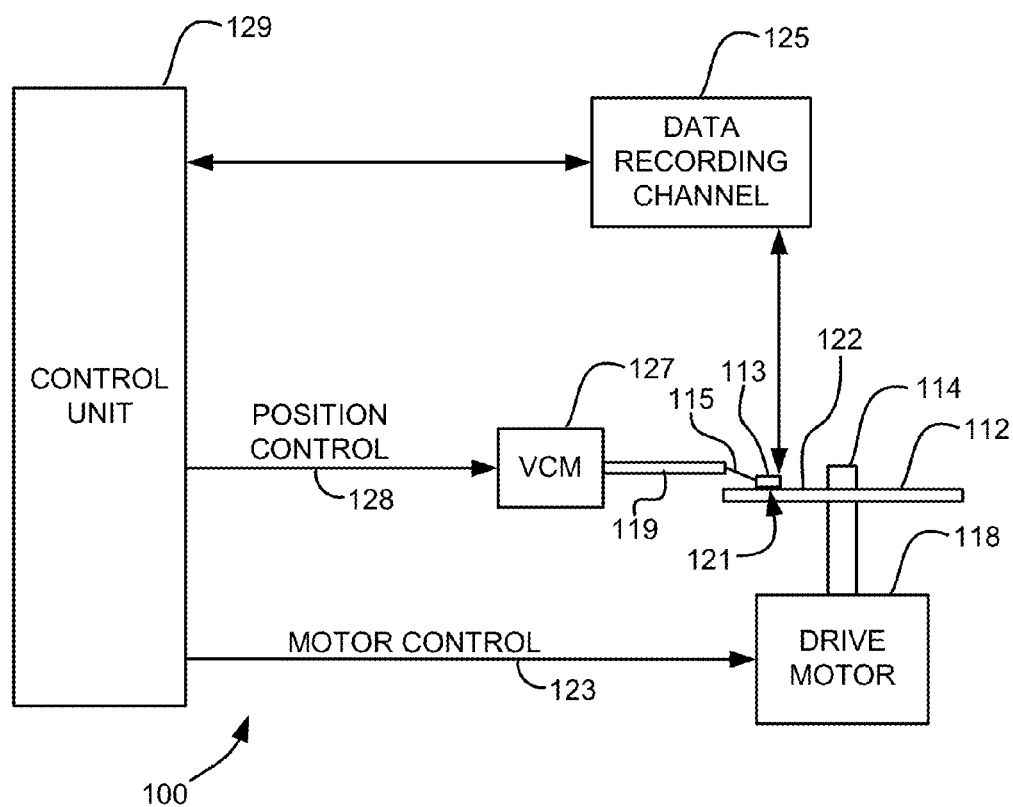
FIG. 1 is a simplified drawing of a magnetic recording disk drive system.

The following description is made for the purpose of illustrating the general principles of the present invention and is not meant to limit the inventive concepts claimed herein. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc.

It must also be noted that, as used in the specification and the appended claims, the singular forms "a," "an" and "the" include plural referents unless otherwise specified.

The following description discloses several preferred embodiments of disk-based storage systems and/or related systems and methods, as well as operation and/or component parts thereof.

In antiferromagnetic (AF) mode oscillation, when $(B_s t)_{RL}$ is made small, the relationship of $(B_s t)_{FGL} > (B_s t)_{RL}$ becomes strong, and oscillations may be considered as small-current oscillations. In a trial-manufactured microwave-assisted magnetic recording (MAMR) head, when the reference layer (RL) film was made thin with the object of obtaining a spin torque oscillator (STO) that would be capable of operation with small current, oscillation of the STO was not achieved when the film thickness was too thin. The STO oscillation characteristics were studied in detail by Landau-Lifshitz-Gilbert (LLG) simulation, and it appeared that in the cycle in which magnetization fluctuation of the field generation layer (FGL) is transmitted to the RL film and the magnetization fluctuation of the RL film returns to the FGL, when the RL film is thin, the fluctuation is amplified and oscillation may not be maintained.

According to one general embodiment, a device includes a main magnetic pole positioned at a media facing surface of the device, the main magnetic pole being configured to generate a writing magnetic field for storing information to magnetic recording media, and a STO positioned adjacent the main magnetic pole, the STO being configured to generate a high-frequency magnetic field to assist in storing the information to the magnetic recording media, wherein the STO includes: a FGL including at least one magnetic film having an easy magnetization plane effectively in a film plane, wherein a magnetization of the FGL is capable of in-plane rotation, a reference layer having a magnetization that is capable of free in-plane rotation, and a stabilizing layer (STL) positioned on a side of the FGL opposite the reference layer, the STL including a magnetic film having an easy magnetization plane effectively in a film plane, wherein a magnetization of the STL is capable of in-plane rotation, and wherein a product of a saturation magnetization of the STL multiplied by a thickness of the STL is less than half a product of a magnetization of the FGL multiplied by a thickness of the FGL.

In another general embodiment, a device includes a main magnetic pole positioned at a media facing surface of the device, and a STO positioned adjacent the main magnetic pole, wherein the STO includes: a FGL including at least one magnetic film having an easy magnetization plane effectively in a film plane, wherein a magnetization of the FGL is capable of in-plane rotation, a reference layer having a magnetization that is capable of free in-plane rotation, and a stabilizing layer (STL) positioned on a side of the FGL opposite the reference layer, the STL including a magnetic film having an easy magnetization plane effectively in a film plane, wherein a magnetization of the STL is capable of in-plane rotation.

According to another general embodiment, a device includes a main magnetic pole positioned at a media facing surface of the device, the main magnetic pole being configured to generate a writing magnetic field for storing information to magnetic recording media, and a STO positioned adjacent the main magnetic pole, the STO being configured to generate a high-frequency magnetic field to assist in storing the information to the magnetic recording media, wherein the STO includes: a reference layer including a Heusler alloy as a majority thereof having a magnetization that is capable of free in-plane rotation, a FGL including at least one magnetic film having an easy magnetization plane effectively in a film plane, wherein a magnetization of the FGL is capable of in-plane rotation, a first non-magnetic spin conducting layer positioned between the reference layer and the FGL, a STL positioned on a side of the FGL opposite the reference layer, the STL including a magnetic film having an easy magnetization plane effectively in a film plane, wherein a magnetization of the STL is capable of in-plane rotation, and a second non-magnetic spin conducting layer positioned between the STL and the FGL, wherein a product of a saturation magnetization of the STL multiplied by a thickness of the STL is less than half a product of a magnetization of the FGL multiplied by a thickness of the FGL, wherein a product of a saturation magnetization of the reference layer multiplied by a thickness of the reference layer is less than half a product of the magnetization of the FGL multiplied by the thickness of the FGL, and wherein a ratio of the thickness of the STL to the saturation magnetization of the STL is greater than about 2 nm/T.

Referring now to FIG. 1, there is shown a disk drive 100 in accordance with one embodiment of the present invention. As shown in FIG. 1, at least one rotatable magnetic medium (e.g., magnetic disk) 112 is supported on a spindle 114 and rotated by a drive mechanism, which may include a disk drive motor 118. The magnetic recording on each disk is typically in the form of an annular pattern of concentric data tracks (not shown) on the disk 112. Thus, the disk drive motor 118 preferably passes the magnetic disk 112 over the magnetic read/write portions 121, described immediately below.

At least one slider 113 is positioned near the disk 112, each slider 113 supporting one or more magnetic read/write portions 121, e.g., of a magnetic head according to any of the approaches described and/or suggested herein. As the disk rotates, slider 113 is moved radially in and out over disk surface 122 so that portions 121 may access different tracks of the disk where desired data are recorded and/or to be written. Each slider 113 is attached to an actuator arm 119 by means of a suspension 115. The suspension 115 provides a slight spring force which biases slider 113 against the disk surface 122. Each actuator arm 119 is attached to an actuator 127. The actuator 127 as shown in FIG. 1 may be a voice coil motor (VCM). The VCM comprises a coil movable within a fixed magnetic field, the direction and speed of the coil movements being controlled by the motor current signals supplied by controller 129.

During operation of the disk storage system, the rotation of disk 112 generates an air bearing between slider 113 and disk surface 122 which exerts an upward force or lift on the slider. The air bearing thus counter-balances the slight spring force of suspension 115 and supports slider 113 off and slightly above the disk surface by a small, substantially constant spacing during normal operation. Note that in some embodiments, the slider 113 may slide along the disk surface 122.

The various components of the disk storage system are controlled in operation by control signals generated by controller 129, such as access control signals and internal clock signals. Typically, control unit 129 comprises logic control circuits, storage (e.g., memory), and a microprocessor. In a preferred approach, the control unit 129 is electrically coupled (e.g., via wire, cable, line, etc.) to the one or more magnetic read/write portions 121, for controlling operation thereof. The control unit 129 generates control signals to control various system operations such as drive motor control signals on line 123 and head position and seek control signals on line 128. The control signals on line 128 provide the desired current profiles to optimally move and position slider 113 to the desired data track on disk 112. Read and write signals are communicated to and from read/write portions 121 by way of recording channel 125.

The above description of a typical magnetic disk storage system, and the accompanying illustration of FIG. 1 is for representation purposes only. It should be apparent that disk storage systems may contain a large number of disks and actuators, and each actuator may support a number of sliders.

An interface may also be provided for communication between the disk drive and a host (integral or external) to send and receive the data and for controlling the operation of the disk drive and communicating the status of the disk drive to the host, all as will be understood by those of skill in the art.

In a typical head, an inductive write portion includes a coil layer embedded in one or more insulation layers (insulation stack), the insulation stack being located between first and second pole piece layers. A gap may be formed between the first and second pole piece layers of the write portion by a gap layer at or near a media facing side of the head (sometimes referred to as an ABS in a disk drive). The pole piece layers may be connected at a back gap. Currents are conducted through the coil layer, which produce magnetic fields in the pole pieces. The magnetic fields fringe across the gap at the media facing side for the purpose of writing bits of magnetic field information in tracks on moving media, such as in circular tracks on a rotating magnetic disk.

The second pole piece layer has a pole tip portion which extends from the media facing side to a flare point and a yoke portion which extends from the flare point to the back gap. The flare point is where the second pole piece begins to widen (flare) to form the yoke. The placement of the flare point directly affects the magnitude of the magnetic field produced to write information on the recording medium.

FIG. 2A illustrates, schematically, a conventional recording medium such as used with magnetic disc recording systems, such as that shown in FIG. 1. This medium is utilized for recording magnetic impulses in or parallel to the plane of the medium itself. The recording medium, a recording disc in this instance, comprises basically a supporting substrate 200 of a suitable non-magnetic material such as aluminum or glass, with an overlying coating 202 of a suitable and conventional magnetic layer.

FIG. 2B shows the operative relationship between a conventional recording/playback head 204, which may preferably be a thin film head, and a conventional recording medium, such as that of FIG. 2A.

FIG. 2C illustrates, schematically, the orientation of magnetic impulses substantially perpendicular to the surface of a recording medium as used with magnetic disc recording systems, such as that shown in FIG. 1. For such perpendicular recording the medium typically includes an under layer 212 of a material having a high magnetic permeability. This under layer 212 is then provided with an overlying coating 214 of magnetic material preferably having a high coercivity relative to the under layer 212.

FIG. 2D illustrates the operative relationship between a perpendicular head 218 and a recording medium. The recording medium illustrated in FIG. 2D includes both the high permeability under layer 212 and the overlying coating 214 of magnetic material described with respect to FIG. 2C above. However, both of these layers 212 and 214 are shown applied to a suitable substrate 216. Typically there is also an additional layer (not shown) called an "exchange-break" layer or "interlayer" between layers 212 and 214.

In this structure, the magnetic lines of flux extending between the poles of the perpendicular head 218 loop into and out of the overlying coating 214 of the recording medium with the high permeability under layer 212 of the recording medium causing the lines of flux to pass through the overlying coating 214 in a direction generally perpendicular to the surface of the medium to record information in the overlying coating 214 of magnetic material preferably having a high coercivity relative to the under layer 212 in the form of magnetic impulses having their axes of magnetization substantially perpendicular to the surface of the medium. The flux is channeled by the soft underlying coating 212 back to the return layer (P1) of the head 218.

FIG. 2E illustrates a similar structure in which the substrate 216 carries the layers 212 and 214 on each of its two opposed sides, with suitable recording heads 218 positioned adjacent the outer surface of the magnetic coating 214 on each side of the medium, allowing for recording on each side of the medium.

Figure 3A:
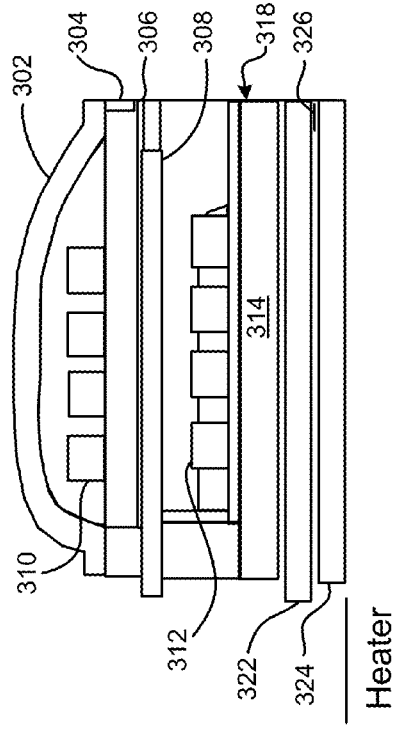
FIG. 3A is a cross-sectional view of one particular embodiment of a perpendicular magnetic head with helical coils.

FIG. 3A is a cross-sectional view of a perpendicular magnetic head. In FIG. 3A, helical coils 310 and 312 are used to create magnetic flux in the stitch pole 308, which then delivers that flux to the main pole 306. Coils 310 indicate coils extending out from the page, while coils 312 indicate coils extending into the page. Stitch pole 308 may be recessed from the media facing side 318. Insulation 316 surrounds the coils and may provide support for some of the elements. The direction of the media travel, as indicated by the arrow to the right of the structure, moves the media past the lower return pole 314 first, then past the stitch pole 308, main pole 306, trailing shield 304 which may be connected to the wrap around shield (not shown), and finally past the upper return pole 302. Each of these components may have a portion in contact with the media facing side 318. The media facing side 318 is indicated across the right side of the structure.

Perpendicular writing is achieved by forcing flux through the stitch pole 308 into the main pole 306 and then to the surface of the disk positioned towards the media facing side 318.

Figure 3B:
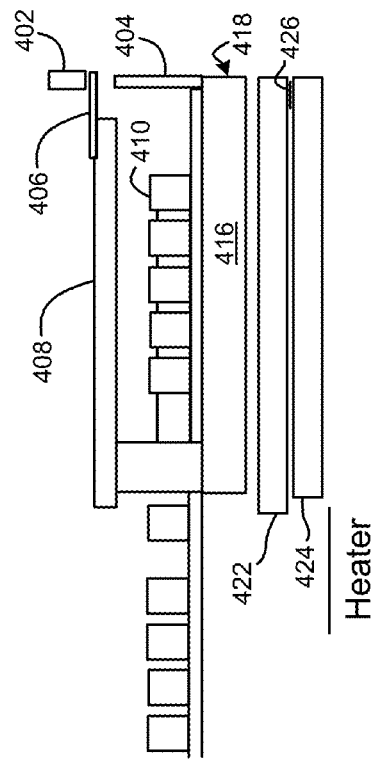
FIG. 3B is a cross-sectional view of one particular embodiment of a piggyback magnetic head with helical coils.

FIG. 3B illustrates a piggyback magnetic head having similar features to the head of FIG. 3A. Two shields 304, 314 flank the stitch pole 308 and main pole 306. Also sensor shields 322, 324 are shown. The sensor 326 is typically positioned between the sensor shields 322, 324.

Figure 4A:
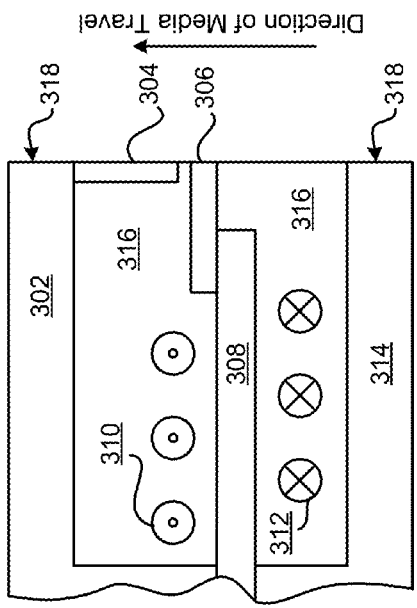
FIG. 4A is a cross-sectional view of one particular embodiment of a perpendicular magnetic head with looped coils.

FIG. 4A is a schematic diagram of one embodiment which uses looped coils 410, sometimes referred to as a pancake configuration, to provide flux to the stitch pole 408. The stitch pole then provides this flux to the main pole 406. In this orientation, the lower return pole is optional. Insulation 416 surrounds the coils 410, and may provide support for the stitch pole 408 and main pole 406. The stitch pole may be recessed from the media facing side 418. The direction of the media travel, as indicated by the arrow to the right of the structure, moves the media past the stitch pole 408, main pole 406, trailing shield 404 which may be connected to the wrap around shield (not shown), and finally past the upper return pole 402 (all of which may or may not have a portion in contact with the media facing side 418). The media facing side 418 is indicated across the right side of the structure. The trailing shield 404 may be in contact with the main pole 406 in some embodiments.

Figure 4B:
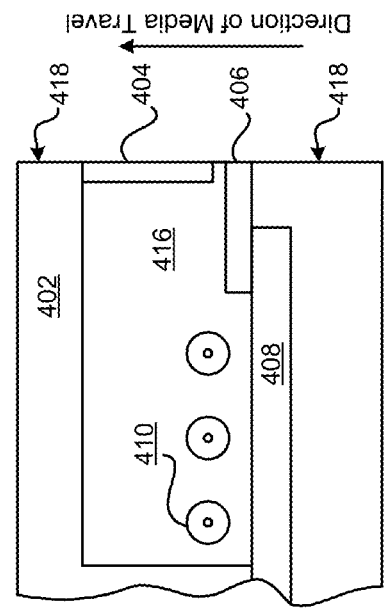
FIG. 4B is a cross-sectional view of one particular embodiment of a piggyback magnetic head with looped coils.

FIG. 4B illustrates another type of piggyback magnetic head having similar features to the head of FIG. 4A including a looped coil 410, which wraps around to form a pancake coil. Also, sensor shields 422, 424 are shown. The sensor 426 is typically positioned between the sensor shields 422, 424.

In FIGS. 3B and 4B, an optional heater is shown away from the media facing side of the magnetic head. A heater (Heater) may also be included in the magnetic heads shown in FIGS. 3A and 4A. The position of this heater may vary based on design parameters such as where the protrusion is desired, coefficients of thermal expansion of the surrounding layers, etc.

Except as otherwise described herein, the various components of the structures of FIGS. 3A-4B may be of conventional materials and design, as would be understood by one skilled in the art.

Figure 5:
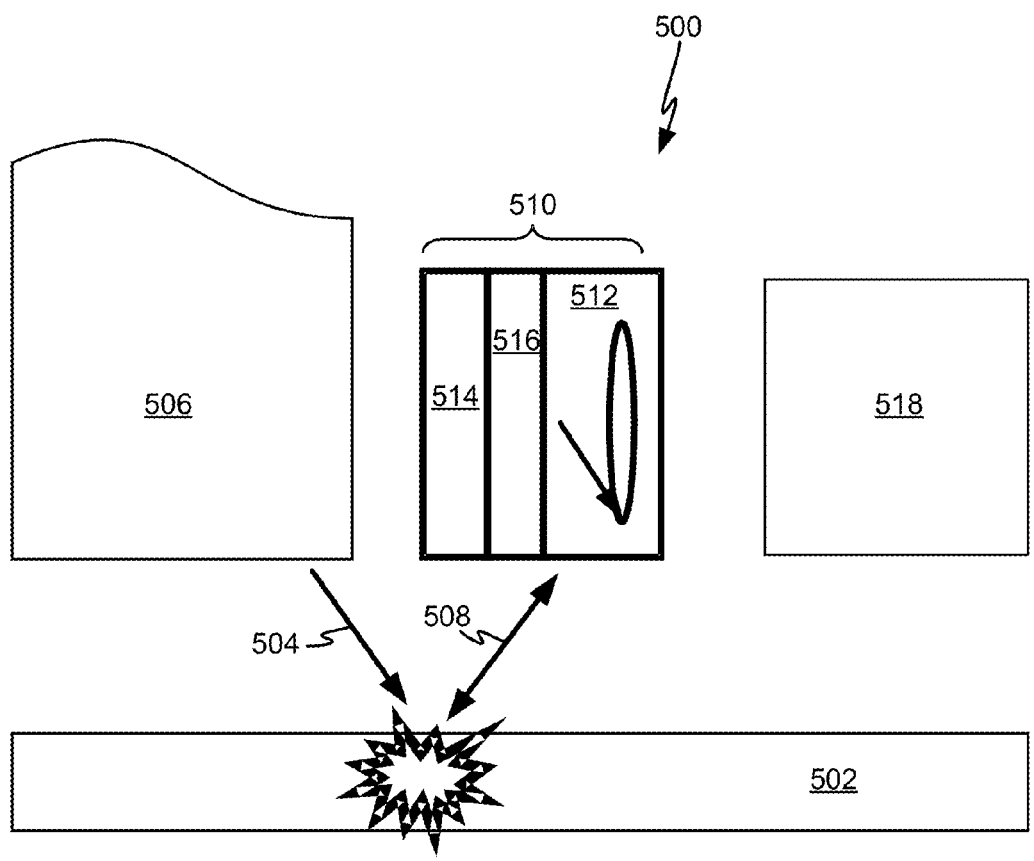
FIG. 5 shows a microwave assisted magnetic recording (MAMR) head.

Now referring to FIG. 5, in order to avoid the problem of overcoming the large magnetic anisotropy $K_u$ of magnetic media, microwave-assisted magnetic recording (MAMR) has been used. In MAMR, as shown in FIG. 5, recording is performed to a magnetic recording medium 502 of large magnetic anisotropy $K_u$ using a write magnetic field 504 which emanates from the main magnetic pole 506 of the perpendicular magnetic recording head 500, in addition to a high-frequency magnetic field 508 generated from a spin torque oscillator (STO) 510 arranged near and/or adjacent to the main magnetic pole 506. This lowers the magnetization reversal field required to flip the bits of the magnetic recording medium 502 by producing thermal fluctuation of magnetization, with the recording region in a magnetic resonance condition. In this way, recording onto the microwave-affected region may be achieved with a magnetic recording medium 502 configured for high recording density exceeding 1 Tb/in$^2$, which is difficult to record with a conventional magnetic head, because the recording magnetic field which is typically provided is insufficient. The magnetic head 500 may also comprise an auxiliary or sub pole 518 positioned on an opposite side of the STO 510 from the main magnetic pole 506.

With MAMR, since a magnetic recording system is used in which magnetization reversal is produced, using the write magnetic field 504 and high-frequency magnetic field 508, by creating magnetic resonance in the recording medium 502, an assisting effect is obtained that becomes larger as the intensity of the high-frequency magnetic field 508 becomes stronger. Therefore, it is anticipated that recording onto a high $K_u$ medium configured for high recording density may be achieved.

When an STO 510 is utilized in MAMR, the high-frequency magnetic field 508 is created by alternately switching the in-plane magnetic load on the side of the field generation layer (FGL) 512 of the layers of the stack (STO 510), whose magnetization is rotating, due to the action of the spindle. A method is shown, known as antiferromagnetic (AF) coupling mode oscillation. In AF coupling mode oscillation, an oscillating condition in which an antiparallel condition of the FGL 512 magnetization and reference layer (RL) 514 magnetization is maintained while rotating the magnetizations. This oscillating condition is produced by spin torque action generated by passing current to the FGL 512 that generates a high-frequency magnetic field, since the RL 514 and FGL 512 are separated by a non-magnetic spin conducting material layer 516 (which typically comprises Cu, etc.).

The principle of AF mode conservation exploits a condition where, even though the direction of the spin torque magnetic field $H_{stq\text{-}FGL}$ that acts on the magnetization $m_{FGL}$ of the FGL 512 and the spin torque magnetic field $H_{stq\text{-}RF}$ that acts on the magnetization $m_{RL}$ of the RL 514 have the same direction, they are typically of different magnitude. $H_{stq\text{-}FGL}$ is shown in Equation 1, while $H_{stq\text{-}RF}$ is shown in Equation 2.

$$H_{stq-FGL} = (m_{FGL} \times m_{RL}) \frac{CJ}{(B_s t)_{FGL}} g_{AF} \quad \text{Equation 1}$$

$$H_{stq-ref} = (m_{FGL} \times m_{RL}) \frac{CJ}{(B_s t)_{RL}} g_{AF} \quad \text{Equation 2}$$

In these equations, $m_{FGL}$ and $m_{RL}$ are the unit magnetization vectors of the FGL 512 and RL 514, respectively, and $(B_s t)_{FGL}$, $(B_s t)_{RL}$ are the products of the film thickness and saturation magnetization of the FGL 512 and RL 514, respectively. J is the current density in the direction perpendicular to the stacking plane of the STO 510. The g factor is a variable that depends on the polarizability (P) and the angle of magnetization. In the case of AF mode oscillation, the FGL 512 and RL 514 are substantially antiparallel, so this factor is identified as $g_{AF}$.

When the apparatus is designed in such a way that $(B_s t)_{FGL} > (B_s t)_{RL}$, then the following condition is created, $H_{stq\text{-}FGL} < H_{stq\text{-}RF}$, i.e., the change in the pursuing magnetization of the FGL 512 is slow, and so it is not able to catch up with the magnetization of the RL 514, which it is trying to follow. However, it should be noted that the spindle magnetic field depends on the outer product of $m_{FGL}$ and $m_{RL}$, and so ceases to act when the antiparallel condition is reached. Consequently, rotation of the FGL 512 magnetization and RL 514 magnetization continues about the applied magnetic field, while maintaining a substantially antiparallel condition. When the FGL 512 magnetization and RL 514 magnetization reach an antiparallel condition, the g factor becomes extremely large ($g_{AF} \gg g$), so an advantage is obtained that a large spin torque effect is achieved for a comparatively small current.

The smaller the drive current of the STO 510 is, the less amount of electron migration occurs. This is advantageous in terms of element life. It has already been recognized that in order to achieve a lowering of current, it is effective to reduce the product magnetization multiplied by film thickness of the RL 514. However, effective ways of accomplishing this have been elusive, since magnetization of the RL 514 becomes unstable and is not able to maintain an oscillation when the product of magnetization multiplied by the film thickness of the RL 514 is lowered too much.

Figure 6:
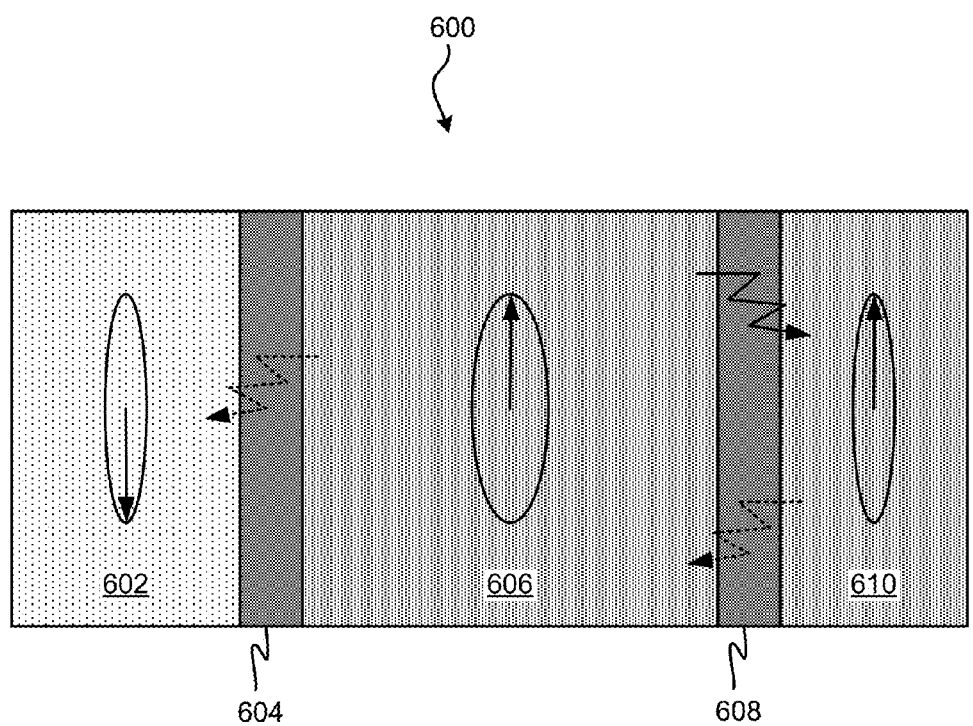
FIG. 6 shows a spin torque oscillator (STO) with a stabilizing layer (STL) according to one embodiment.

Various computer simulations, using the Landau-Lifshitz-Gilbert (LLG) equation, of methods of producing FGL oscillation were performed even when the product of magnetization and film thickness of the RL is small. From these computer simulations, it was determined that in order to operate effectively in this scenario, a fluctuation suppression layer, referred to as a stabilizing layer (STL), may be provided in a STO, as shown in FIG. 6. As shown in FIG. 6, the STO 600 comprises, from left to right, a RL 602, a first non-magnetic spin conduction spacer layer 604, the FGL 606, a second non-magnetic spin conduction spacer layer 608, and the before-mentioned STL 610.

It is believed that fluctuation generated in the FGL 606 is readily transmitted to the STL 610 from the RL 602, and the FGL 606 is thereby stabilized. The conditions of the oscillation characteristic of an STO 600 provided with an STL 610 were then studied using the following LLG equations.

$$\frac{dm_{STL}}{dt} =$$
$$-\gamma m_{FGL} \times H_{STL} + \alpha_{STL} m_{STL} \times \frac{dm_{STL}}{dt} - \gamma \beta_{S-FS} J \cdot m_{STL} \times (m_{STL} \times m_{FGL})$$

$$\frac{dm_{FGL}}{dt} = -\gamma m_{FGL} \times H_{FGL} + \alpha_{FGL} m_{FGL} \times \frac{dm_{FGL}}{dt} -$$
$$\gamma J \cdot m_{FGL} \times (\beta_{F-FS}(m_{STL} \times m_{FGL}) + \beta_{F-FR}(m_{FGL} \times m_{RL}))$$

$$\frac{dm_{RL}}{dt} = -\gamma m_{RL} \times H_{RL} + \alpha_{RL} m_{RL} \times \frac{dm_{RL}}{dt} -$$
$$\gamma \beta_{R-FR} J \cdot m_{RL} \times (m_{FGL} \times m_{RL}),$$

$$\beta_{F-FS} = \frac{\pi \mu_B}{2500 \gamma e (B_s t)_{FGL}} g_{FS},$$

$$\beta_{S-FS} = \frac{\pi \mu_B}{2500 \gamma e (B_s t)_{STL}} g_{FS},$$

$$g_{FS} = \left[-4 + \frac{(1 + P_{FS})^3 (3 + m_{FGL} \cdot m_{STL})}{4 P_{FS}^{3/2}}\right]^{-1}$$

$$\beta_{F-FR} = \frac{\pi \mu_B}{2500 \gamma e (B_s t)_{FGL}} g_{FR},$$

$$\beta_{R-FR} = \frac{2 \mu_B}{2500 \gamma e (B_s t)_{RL}} g_{FR},$$

$$g_{FR} = \left[-4 + \frac{(1 + P_{FR})^3 (3 + m_{FGL} \cdot m_{RL})}{4 P_{FR}^{3/2}}\right]^{-1}$$

Figure 7:
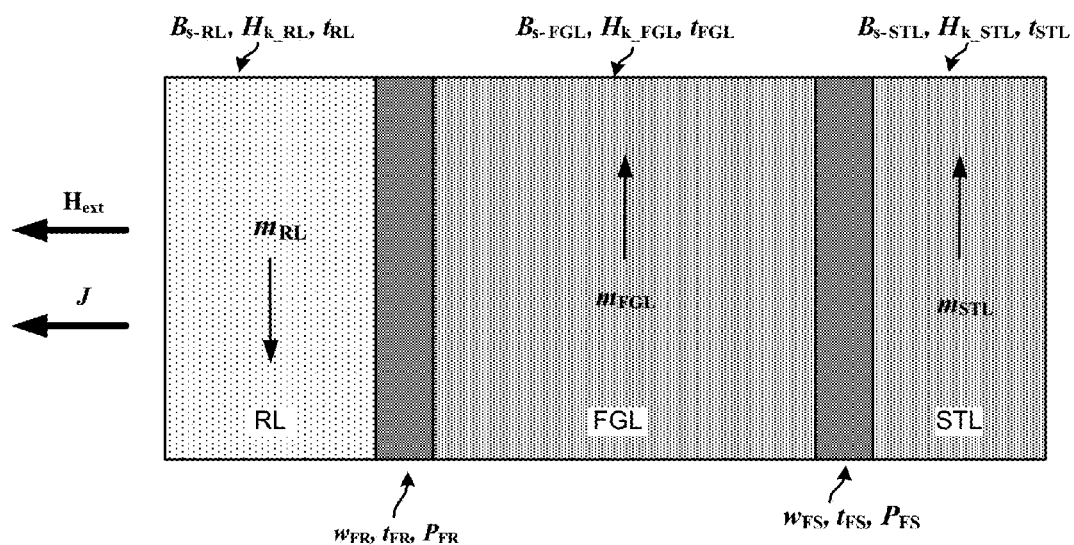
FIG. 7 shows LLG equation explanations for an STO in one embodiment.

Using FIG. 7 as a guide, in the LLG equations shown above, $m_{STL}$, $m_{FGL}$, and $m_{RL}$ are the unit magnetization vectors of the STL, FGL, and RL, respectively, $H_{STL}$, $H_{FGL}$, and $H_{RL}$ are the effective magnetic fields of the STL, FGL, and RL, respectively, $\alpha_{STL}$, $\alpha_{FGL}$, and $\alpha_{RL}$ are the damping constants of the STL, FGL, and RL, respectively, and $(B_s t)_{STL}$, $(B_s t)_{FGL}$, and $(B_s t)_{RL}$ are the products of the magnetization and the film thickness of the STL, FGL, and RL, respectively. The effective magnetic fields considered were the magnetic anisotropy magnetic field, the exchange coupling magnetic field, the magnetostatic field, and the external magnetic field. J is the current density in the direction perpendicular to the stacking layer plane of the STO; P is the polarizability, and $\gamma$, $\pi$, $\mu_B$, and e are the gyromagnetic constant, pi, the Bohr magneton, and unit electric charge, respectively.

Using the LLG equations, oscillation of an STO having a cross-sectional shape of 40 nm×40 nm was studied. The saturation magnetization (Bs_RL) and the film thickness (t_RL)

of the RL were set to be 1.2T and 3.0 nm, respectively; the saturation magnetization (Bs_FGL) and the film thickness (t_FGL) of the FGL were set to be 2.4T and 8.0 nm, respectively; and the saturation magnetization (Bs_STL) and the film thickness (t_STL) of STL were set to be 0.6T and 1.5 nm, respectively. Also, the exchange interaction (w_FR), the film thickness (t_FR), and the polarizability (P_FR) between the RL and the FGL were respectively set as 0, 3.0 nm, and 0.244, respectively; and the exchange interaction (w_FS), the film thickness (t_FS), and the polarizability (P_FS) between the STL and the FGL were set as 1 erg/cm$^2$, 0.8 nm, and 0.244, respectively. The magnetic anisotropy of the magnetic film was assumed to be 0 in all cases.

Figure 8:
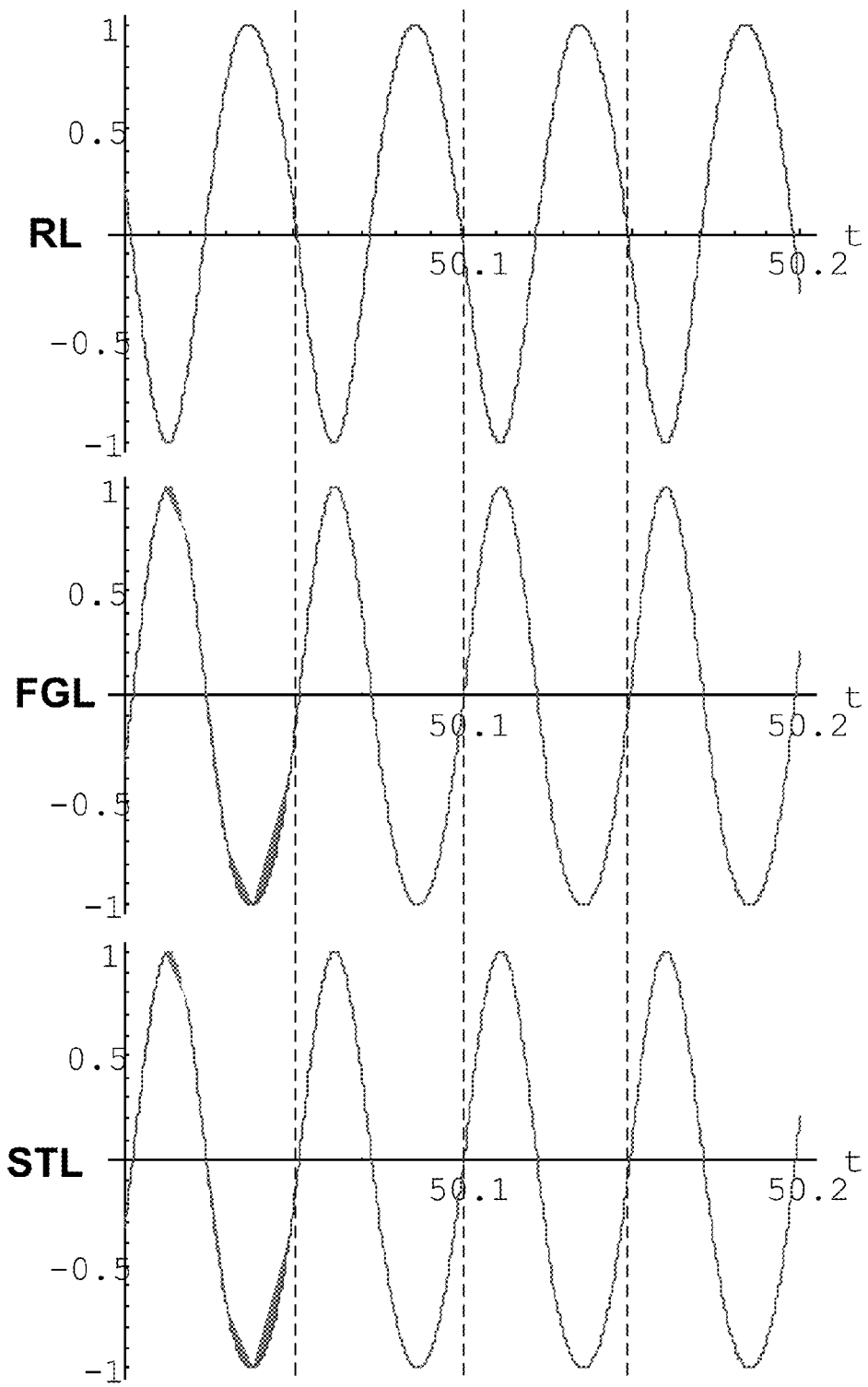
FIG. 8 shows operational responses of one embodiment of an STO.

FIG. 8 shows change with time of the normalized in-plane magnetization of each layer (RL, FGL, STL), when the external magnetic field is $H_{ext}$=10 kOe, and when ample current is supplied. The magnetizations of each of the layers rotate in synchronization, but the RL is in opposite phase to the FGL and so rotates substantially in antiparallel with the FGL. In contrast, the STL and the FGL are substantially in phase and rotate facing the same direction.

Figure 9A:
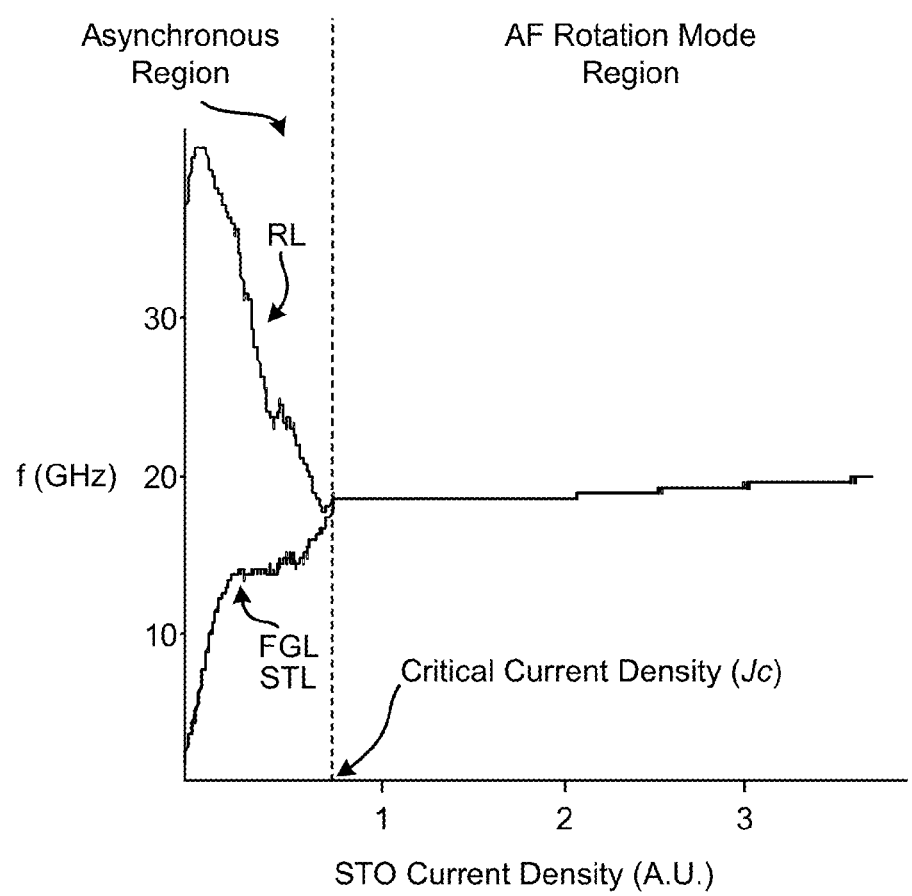
FIG. 9A shows oscillation characteristics of an STO according to one embodiment.

When the current is insufficient, the RL and the FGL are not synchronized. FIG. 9A shows STO current density dependence of the oscillation frequency in accordance with testing conducted on a STO. The frequency was averaged at 1 ns intervals. The magnetization of the FGL and STL are synchronized, irrespective of current density. However, the RL has a different frequency to that of the FGL below a certain current density (referred to herein as the critical current density, Jc), and thus is not synchronized with the FGL below this critical current density. In this unsynchronized oscillation condition, the frequency of the FGL is affected by the RL, so a stable high-frequency magnetic field is not obtained. Therefore, reduction of the critical current density, Jc, may alleviate this issue.

Figure 9B:
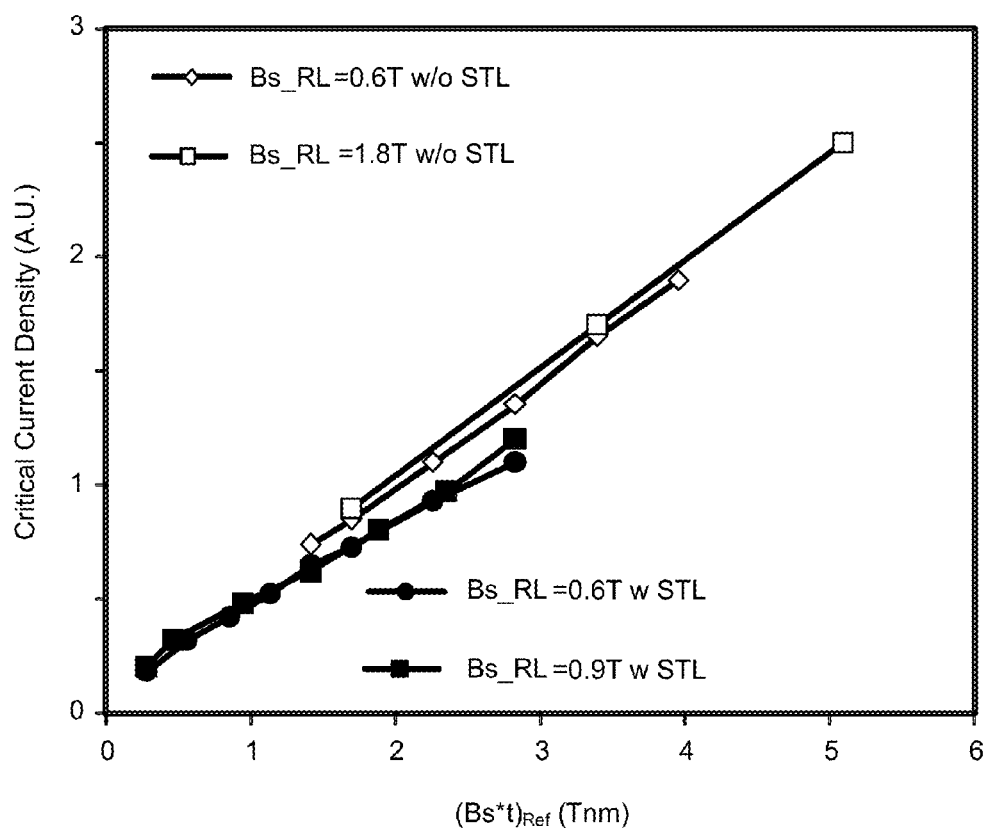
FIG. 9B shows oscillation characteristics of an STO according to one embodiment.

FIG. 9B shows the result of determining Jc by varying the magnetization*film thickness product of RL, where a stabilizing layer (STL) according to one embodiment is provided in the STO, and where no such layer is provided in the STO. The saturation magnetization (Bs_STL) and the film thickness (t_STL) of the STL were set as 0.5T and 1.5 nm, respectively. The saturation magnetization (Bs_FGL) and the film thickness (t_FGL) of the FGL were set as 2.3T and 8.0 nm, respectively. The exchange interaction (w_FR), the film thickness (t_FR), and the polarizability (P_FR) between the RL and the FGL were set as 0, 2.0 nm, and 0.244, respectively; the exchange interaction (w_FS), the film thickness (t_FS), and the polarizability (P_FS) between the STL and the FGL were set as 1 erg/cm$^2$, 0.8 nm, and 0.244, respectively. The magnetic anisotropy of the magnetic film was assumed to be 0 in all cases. When no STL was employed, of the parameters referred to above, those relating to the STL were all set as 0.

When the magnetization*film thickness product of RL is made smaller, this makes it possible to reduce the critical current. However, with the conventional construction, if this product is made too small, fluctuations generated in the FGL are amplified, giving rise to a problem where oscillation is stopped and the device is rendered useless. It is concluded that, when a fluctuation suppressing layer (STL) is provided in the FGL, the FGL is stabilized, making further reductions in the critical current possible.

Figure 11:
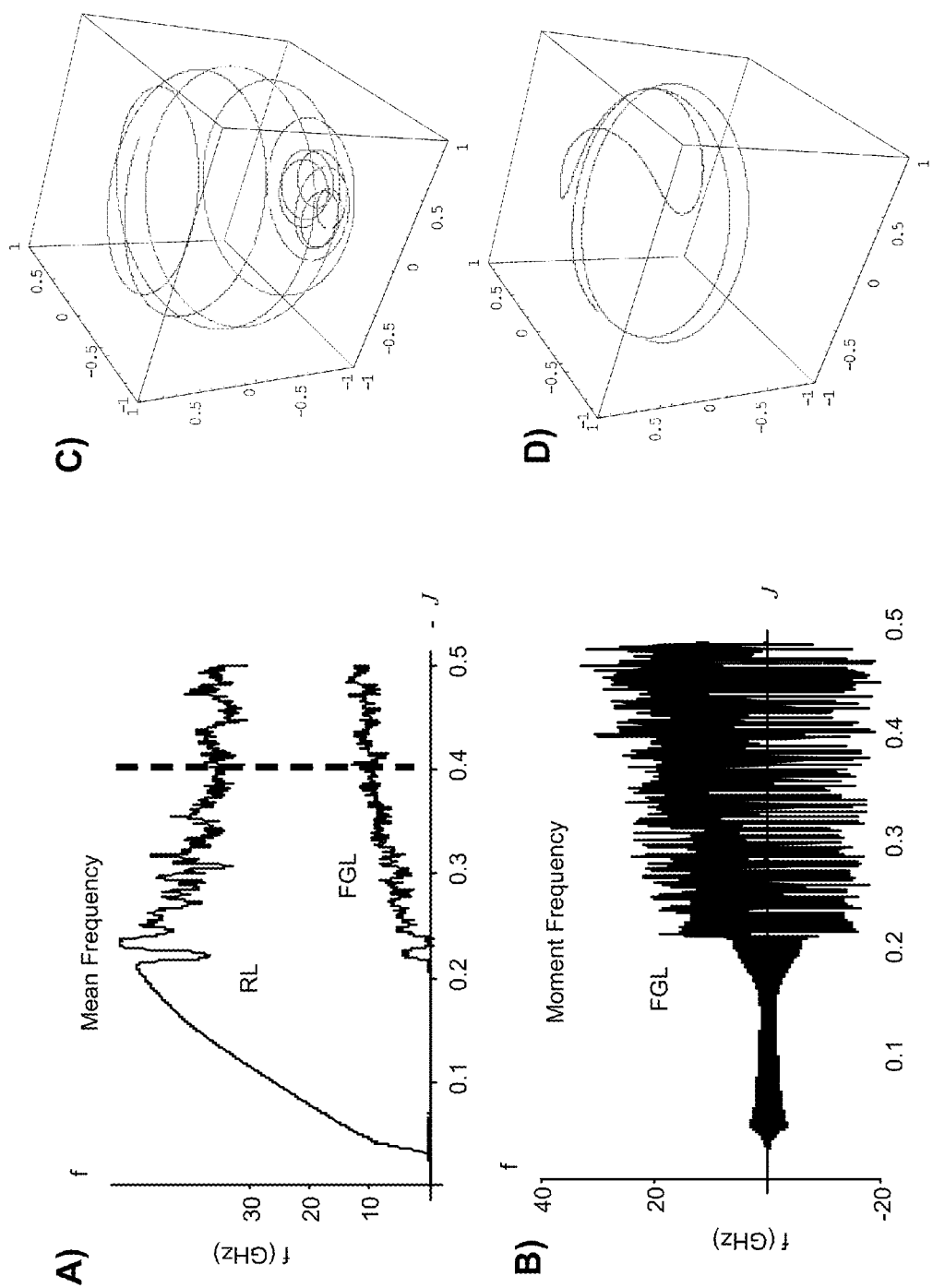
FIG. 11 shows oscillation characteristics of a conventional STO without a STL.
Figure 12:
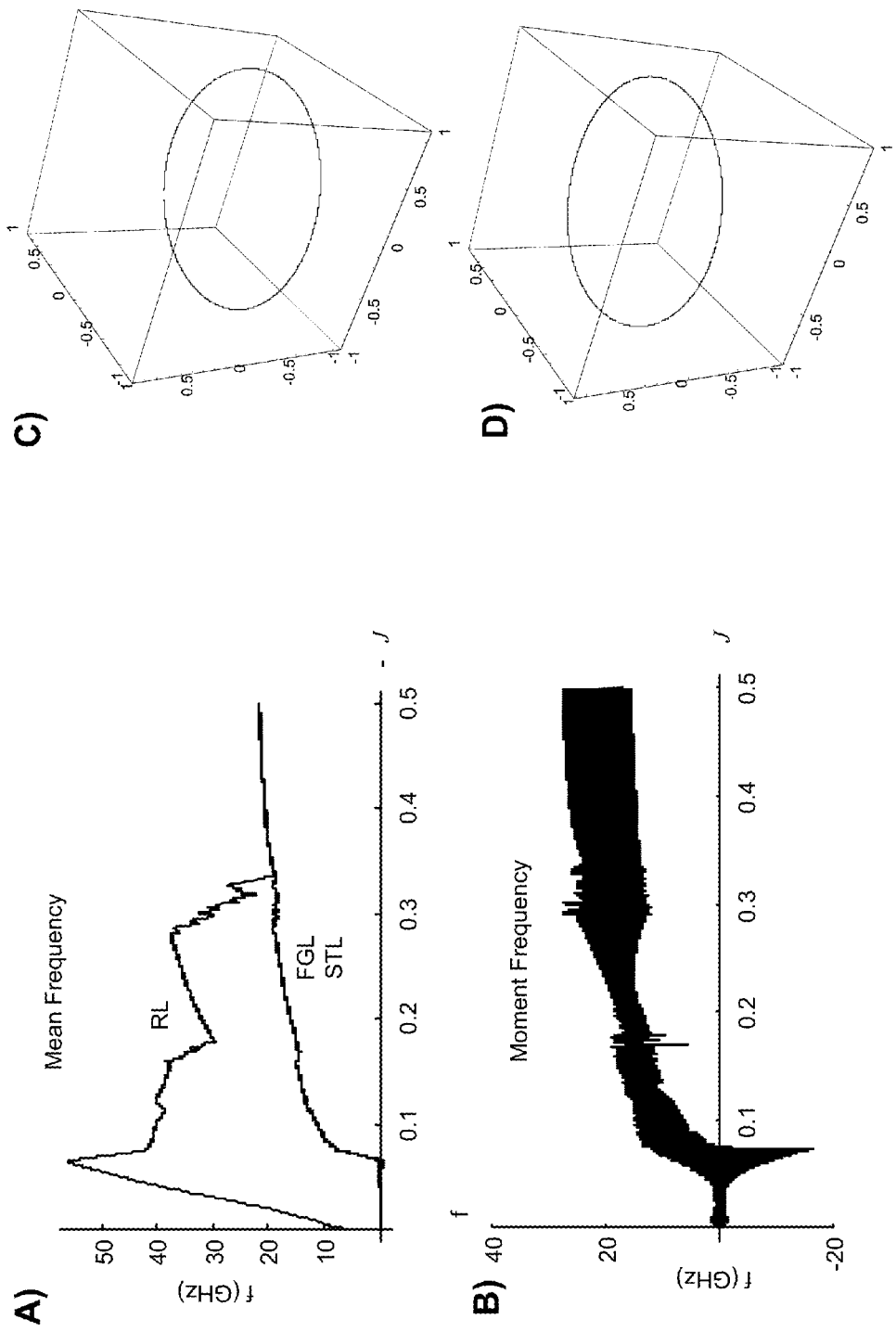
FIGS. 12A-12D show oscillation characteristics of an STO with a STL according to one embodiment.

Other beneficial effects of embodiments using the STL will now be described with reference to FIGS. 11A-12D. In the non-synchronized rotation condition on the low-current side, the average frequencies of the FGL and the stabilizing layer (STL) are different, so there is considerable rotational fluctuation. FIG. 11A shows the STO current density dependence of the average frequency, and FIG. 11B shows the instantaneous frequency of a conventional STO. The saturation magnetization (Bs_FGL) and the film thickness (t_FGL) of the FGL were set as 2.3T and 6.0 nm, respectively, and the saturation magnetization (Bs_RL) and the film thickness (t_RL) of RL were set as 1.1 T and 2.5 nm, respectively. The exchange interaction (w_FR), the film thickness (t_FR), and the polarizability (P_FR) between the RL and the FGL were set as 0, 2.0 nm, and 0.27, respectively. For the magnetic layer, a soft magnetic layer was employed.

The instantaneous frequency was determined by the phase change of the in-plane magnetization component of the FGL, at 0.01 ns intervals. Even when the average frequency is a positive value, when the instantaneous frequency is a negative value, this indicates that the magnetization is temporarily performing reverse rotation. FIG. 11C shows the way in which magnetization rotation takes place at J=0.4 in three dimensions, while FIG. 11D shows the way in which magnetization rotation takes place when an external magnetic field is applied from above (11 kOe). It can be seen that the FGL magnetization (in FIG. 11D) performs reverse rotation once in several rotations, the amount of such reverse rotation being about ⅓.

When the FGL performs reverse rotation, the direction of rotation of the high-frequency magnetic field that is exerted on the recording medium is reversed, i.e., it becomes opposite to the precession motion of the medium magnetization, so the MAMR effect is not obtained. The RL magnetization (as shown in FIG. 11C) appears to rotate in the magnetization direction, while displaying considerable fluctuation.

FIGS. 12A-12B show the average frequency and instantaneous frequency of an STO in which a stabilizing layer (STL) is employed in a STO construction as shown in FIG. 6. The saturation magnetization (Bs_STL) and the film thickness (t_STL) of the STL were set as 1.0T and 3.0 nm, respectively, and the exchange interaction (w_FS), film thickness (t_FS), and polarizability (P_FS) between the STL and the FGL were set as 1 erg/cm$^2$, 0.8 nm, and 0.27, respectively. As the magnetic layer, a soft magnetic layer was employed. The average frequencies of the FGL and RL are different until J=0.33 is exceeded, so a non-synchronized rotation condition is produced.

In contrast, the average frequencies of the FGL and STL are the same, irrespective of the current density. When the oscillation initiation current density (in this case, J=0.07) of the FGL is exceeded, the instantaneous frequency assumes a negative value. FIGS. 12C-12D show magnetization rotation in three dimensions where J=0.2. The RL magnetization (as shown in FIG. 12C) and the FGL magnetization (as shown in FIG. 12D) both follow substantially stable circular orbits. Therefore, it appears that, even when the STO current density is below Jc, the effect on the MAMR effect is not particularly great. Therefore, FGL magnetization oscillation is stabilized by employing an STL and a MAMR effect may be expected even when the current density does not exceed Jc.

Figure 13:
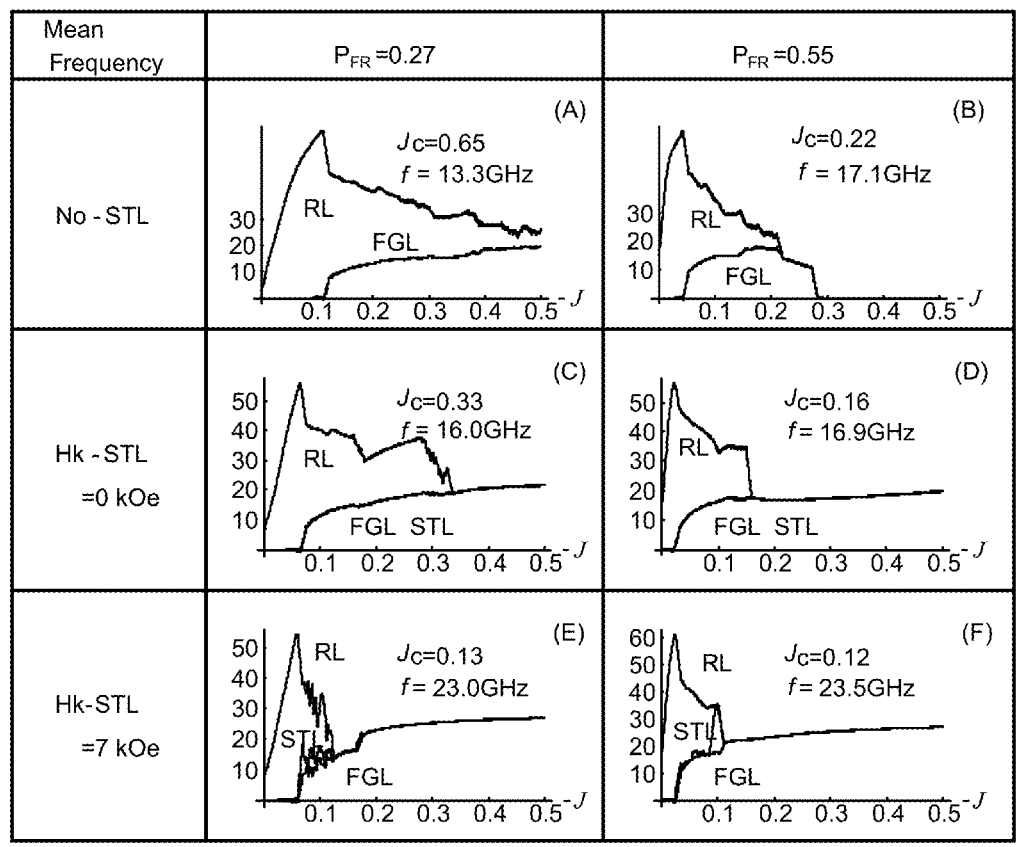
FIG. 13 shows beneficial effects of using an STO according to various embodiments.

The beneficial effect of another embodiment is described with reference to FIG. 13. FIG. 13 shows the STO current density dependence of the oscillation frequency of the various magnetic layers, for various STO constructions. In the conventionally constructed STO(A), the saturation magnetization (Bs_FGL) and the film thickness (t_FGL) of the FGL were respectively 2.3 T and 6.0 nm; the saturation magnetization (Bs_RL) and the film thickness (t_RL) of RL were respectively 1.1 T and 0.8 nm; and the exchange interaction (w_FR) and film thickness (t_FR) between the RL and the FGL were respectively 0 and 2.0 nm. The polarizability (P_FR) between the FGL and the RL was assumed to be 0.27. When STLs are included in the construction, interposition of a Cu film of film thickness (t_FS) of 0.8 nm, and a magnetic material (C) having soft magnetic properties or a magnetic material (E) having perpendicular magnetic anisotropy of 7 kOe were added. It is assumed that this would result in an exchange interaction (w_FS) of 1 erg/cm$^2$ and a polarizability (P_FS) of 0.37 between the FGL and the STL. Also, with regard to the respective constructions, the oscillation performance of some cases (B, D, and F), in which the polarizability (P_FR) between the FGL and RL was 0.55 were studied.

As already described, the problem with the STO(A) of the conventional construction is that Jc is large, so unless a large current density exceeding Jc is supplied, a sufficient MAMR effect is not obtained. If a large current density is supplied, degradation of the element tends to occur, due to, for example, generation of heat and/or migration. However, according to one embodiment, it is possible to considerably lower Jc, by providing (C) a stabilizing layer (STL). However, thinking in terms of a STO, if merely lowering the Jc is in question, the spin torque could be intensified (B) by increasing the polarizability, P. However, with an STO of conventional construction, this is difficult to implement simply by increasing the polarizability P, since this would result in stopping oscillation when the current density becomes even a little larger than Jc.

In an STO(D) equipped with an STL, a Jc-reduction effect, produced by polarizability adjustment, is first achieved by increasing the polarizability P. An even larger stabilization effect is obtained (E, F) by conferring perpendicular anisotropy on the STL. The chief factors in this effect are thought to be that the demagnetizing field in the orthogonal direction is reduced by application of the perpendicular-direction component of the STL magnetization to the FGL as an exchange magnetic field, and that the FGL magnetization is forced into the plane of rotation by the spindle torque. Also, the high-frequency magnetic field is intensified by an increase of the in-plane component of the FGL magnetization.

More beneficial effects, according to one embodiment, are described with reference to FIG. 14. In MAMR, in order to obtain a high-frequency magnetic field, it is helpful to make the product (Bs*t)_FGL of the magnetization and the film thickness of the FGL large. However, since the magnetic domains develop in the film thickness direction, even when the FGL is of large thickness, exceeding about 6 nm, there is no improvement in the MAMR effect.

It is therefore concluded that using a laminated FGL 1402 (FGL-stack construction) may be effective to produce desired results; however, this introduces the problem that, when the newly laminated (expanded) FGL 1402 (including FGL-1 1404 and FGL-2 1406) is of a thickness exceeding about half the film thickness limit (in this case, 6 nm) of a single-layer FGL, oscillation is not achieved.

It is considered that the cause of this is amplification of magnetization fluctuations between the FGLs 1404, 1406, and therefore addition of a stabilizing layer (STL 1408) may be effective. By the fluctuation-suppressing effect of the STL 1408, the rotation of the laminated FGLs 1404, 1406 may be regularized, so that a strong high-frequency magnetic field is obtained.

Figure 14:
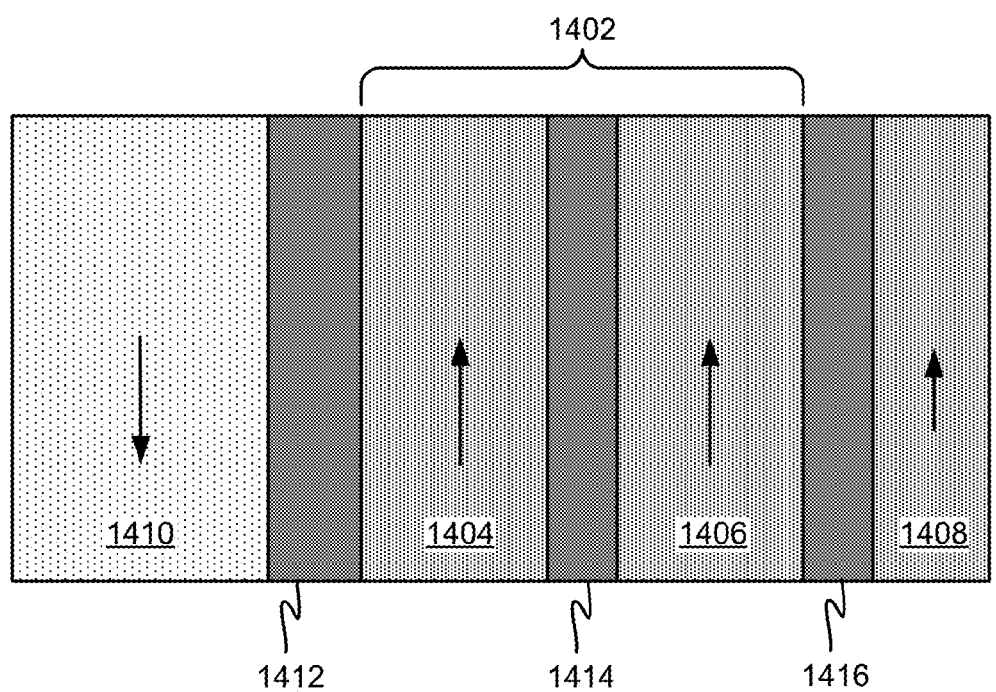
FIG. 14 shows an STO with a FLG stack and a STL according to one embodiment.

Whether oscillation is achieved as in FIG. 14 was verified using the LLG equations. It is assumed that the saturation magnetization (Bs_RL) and the film thickness (t_RL) of the RL 1410 are 1.2 T and 3.0 nm, respectively; the saturation magnetization (BS_FGL1) and film thickness (t_FGL1) of the FGL-1 1404 are 2.3 T and 6.0 nm, respectively, the saturation magnetization (Bs_FGL2) and film thickness (t_FGL2) of the FGL-2 1406 are 2.3 T and 6.0 nm, respectively; the saturation magnetization (Bs_STL) and film thickness (t_STL) of the STL 1408 are 0.6 T and 1.5 nm, respectively, the exchange interaction (w_FR), the film thickness (t_FR), and polarizability (P_FR) between the RL 1410 and FGL-1 1404 are 0, 2.0 nm, and 0.24, respectively; exchange interaction (w_FS), film thickness (t_FS) and polarizability (P_FS) between the STL 1408 and FGL-2 1406 is 1 erg/cm$^2$, 0.8 nm, and 0.24, respectively, the exchange interaction (w_FF), film thickness (t_FF), and polarizability (P_FF) between the FGL-1 1404 and the FGL-2 1406 are 2 erg/cm$^2$, 0.6 nm, and 0.24, respectively. For the magnetic film, soft magnetic material is employed.

The structure may also include a first non-magnetic spin conduction layer 1412, a second non-magnetic spin conduction layer 1414, and a third non-magnetic spin conduction layer 1416, each layer comprising a suitable material known in the art, such as Cu.

In another embodiment, the FGL stack 1402 may comprise more than two FGLs, such as three, four, five, a plurality, etc., each FGL being separated from one another by a spin conduction layer.

Figure 15:
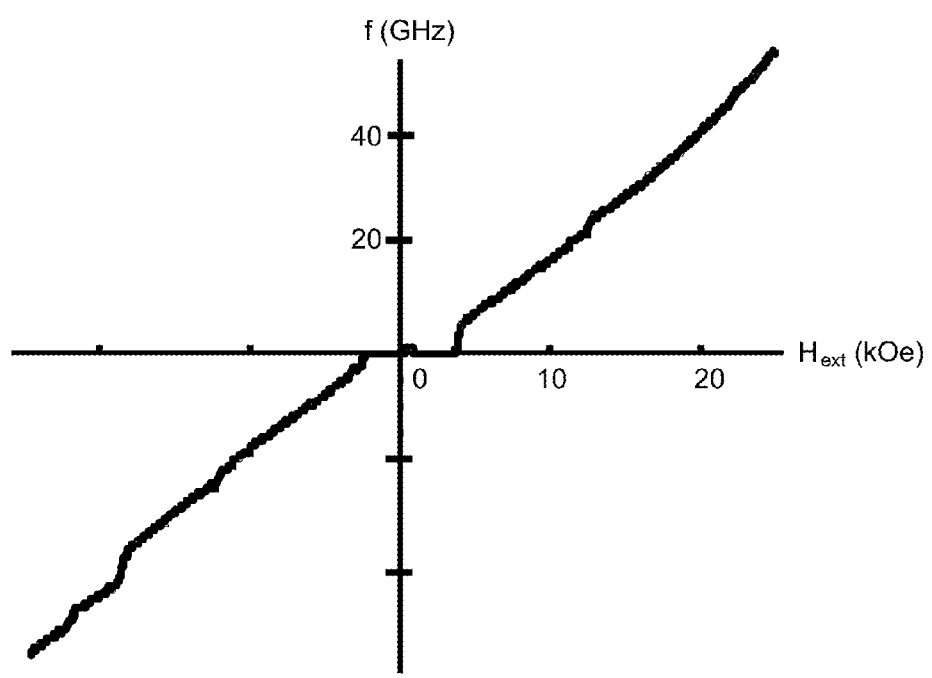
FIG. 15 shows oscillation characteristics of an STO with a STL according to one embodiment.

FIG. 15 shows the oscillation frequency of an STO, plotted against external magnetic field Hext. As seen, excluding the area near the origin (zero), the oscillation frequency is proportional to Hext.

Figure 16:
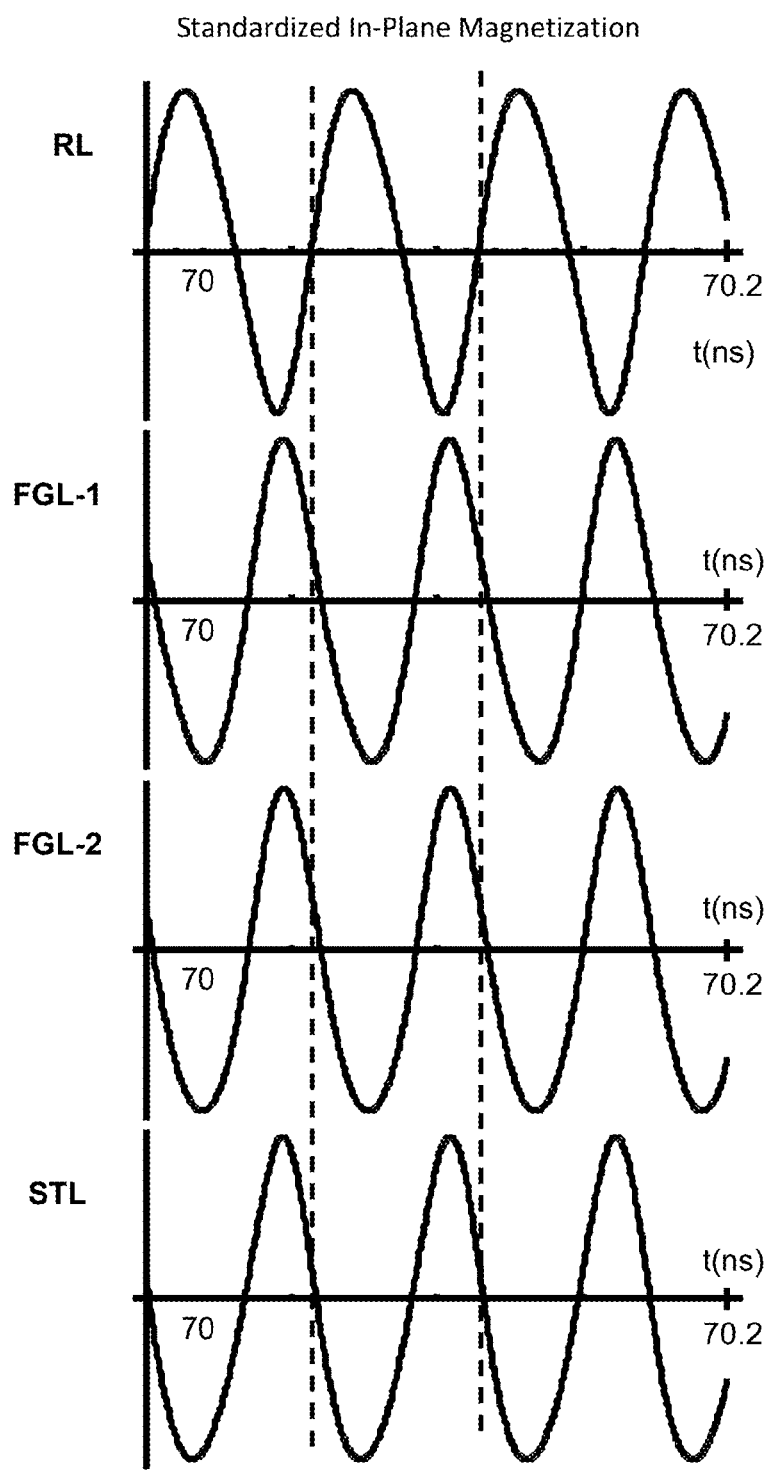
FIG. 16 shows standardized in-plane magnetization of various components of an STO with a FGL stack and a STL according to one embodiment.

FIG. 16 shows change with time of the normalized in-plane magnetization of each layer, when the external magnetic field is Hext=10 kOe. The magnetizations of each of the layers are synchronized: FGL-1, FGL-2, and STL are substantially in the same phase and rotate in the same direction. In contrast, the magnetization of RL is in the opposite phase to that of the FGL, and rotates substantially in antiparallel to that of the FGL. This demonstrates the possibility that intensification of the high-frequency magnetic field may be obtained by unitary rotation (FGL-stack construction) of the FGL-1 and FGL-2, as shown in FIG. 14.

Figure 17:
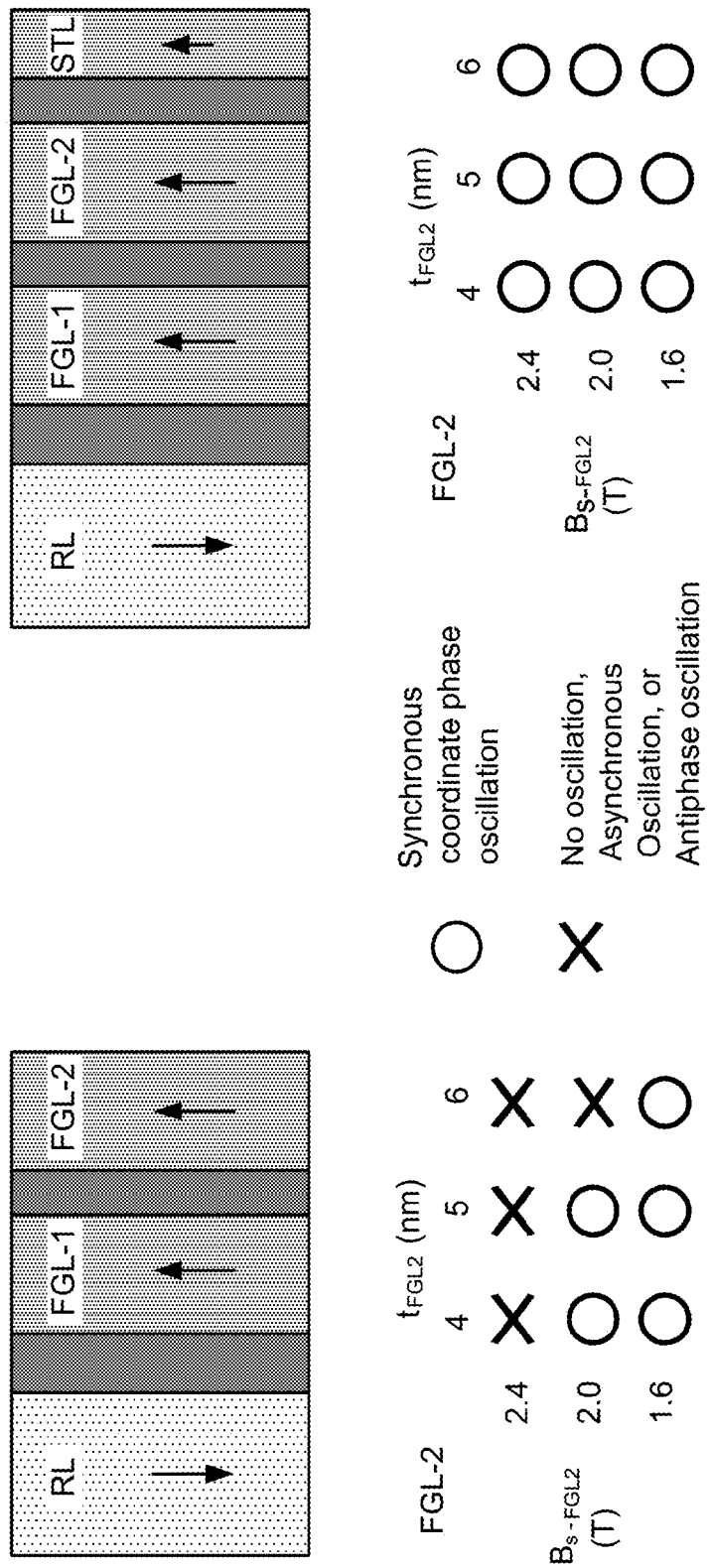
FIG. 17 shows benefits of using a STO with a FGL stack and a STL according to one embodiment.

The benefits of another embodiment are shown in FIG. 17. FIG. 17 shows the relationship of the oscillation condition of FGL-1 and FGL-2 for various STO constructions. In the conventionally constructed STO(A), the saturation magnetization (Bs_FGL1) and the film thickness (t_FGL1) of the FGL-1 were 2.4 T and 6.0 nm, respectively; the saturation magnetization (Bs_RL) and the film thickness (t_RL) of the RL were 1.1 T and 1.5 nm, respectively; and the exchange interaction (w_FR) and film thickness (t_FR) between the RL and the FGL11 were 0 and 3.0 nm, respectively. The polarizability (P_FR) between the FGL and the RL was assumed to be 0.24. The saturation magnetization (Bs_FGL2) and the film thickness (t_FGL2) of the FGL-2 were varied respectively in the ranges of 1.6 to 2.4 T and 4.0 to 6.0 nm. It was assumed that an exchange interaction (w_FS) of 2 erg/cm2 and a polarizability (P_FS) of 0.24 would act between FGL-1 and FGL-2.

STLs were included in (B), with interposition of Cu of film thickness (t_FS) of 0.8 nm, the STLs comprising a magnetic material having soft magnetic properties of 0.6 T with a thickness 2.0 nm. It was assumed that the exchange interaction (w_FS) between the FGL and the STL were be 1 erg/cm2, with a polarizability (P_FS) of 0.24. In FIG. 17, for the combinations of Bs_FGL2 and t_FGL2, cases where FGL-1 and FGL-2 oscillate synchronously in phase is indicated by an O, and cases where no oscillation takes place, asynchronous oscillation, or opposite-phase oscillation are indicated by an X.

With the FGL-stack construction, in order to obtain a strong high-frequency magnetic field, it is desirable that the magnetization*film thickness product of the extension layer (FGL-2) be as close as possible to that of FGL-1. In the conventional construction, in which there is no STL, the magnetization*film thickness product of FGL-2 cannot be increased beyond about 10 T·nm. By using the STL (stabilizing layer), oscillation becomes achievable even with a magnetization*film thickness product of 14.4 T·nm. An STO with an effective thickness of 12 nm with a 2.4 T FGL may be constructed. By using an STL, further extension of the FGL may be achieved.

As described above, the following may be achieved in an STO of conventional construction by: providing a stabilizing layer (STL) on the outside of the field generation layer (FGL) (i.e., the opposite side of the STO from the RL, sandwiching the non-magnetic spin conduction layer therebetween); conferring perpendicular magnetic anisotropy on the STL; and raising the spin polarizability of the RL:

1. Reduction of Jc;
2. Achieving stable FGL oscillation, even below Jc, thereby making microwave-assisted magnetic recording possible;
3. Increase of the oscillation frequency;
4. Intensification of the high-frequency magnetic field; and
5. Intensification of the high-frequency magnetic field, due to the FGL-stack construction.

Due to points 1. and 2. above, extension of the element life and increased reliability, by lowering the STO operating current, may be achieved. Due to points 3., 4., and 5. above, improvement in the assisted recording performance, and assisted recording onto media configured for higher recording densities may be achieved.

Figure 18:
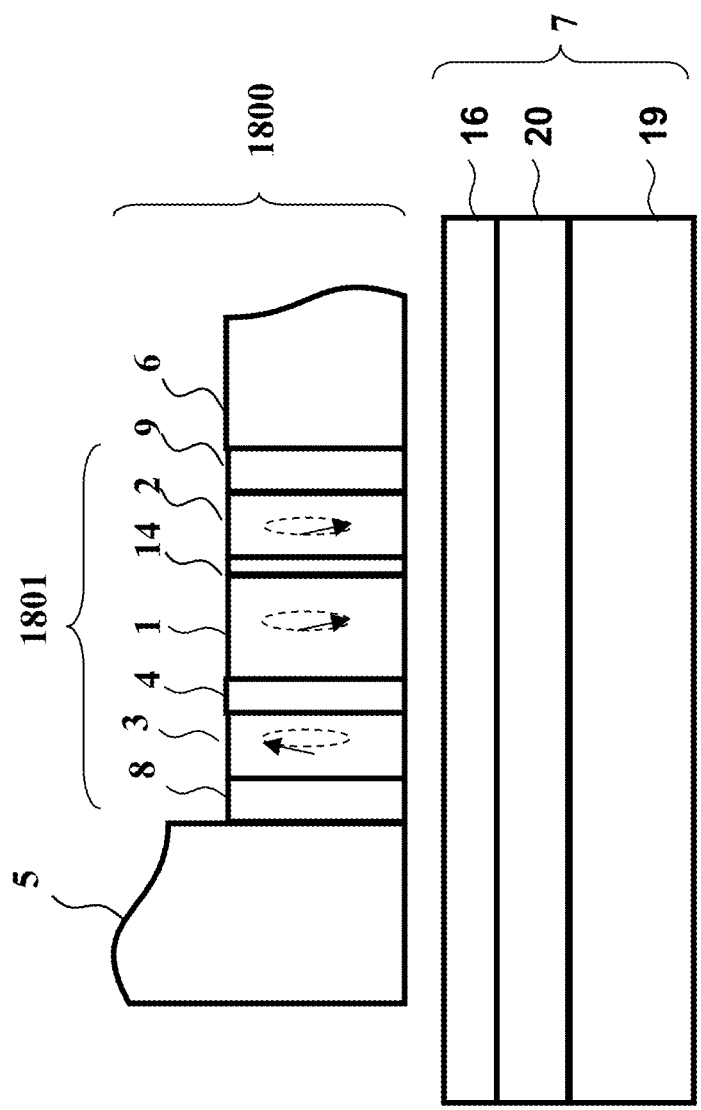
FIG. 18 shows a cross-section of a magnetic head and recording medium according to one embodiment.

Particular characteristics, constructions, and approaches are described in detail with reference to specific embodiments. In FIG. 18, a cross-sectional diagram of a device, such as a magnetic recording head is shown, according to an embodiment, sectioned in a plane that is perpendicular (vertical direction in the Figure) to the recording medium surface parallel with the direction of travel of the head (track direction, which is the left/right direction in the Figure). The cross-section of the medium is also shown in the Figure. For the remainder of this description, the device will be referred to as a recording head.

In regard to the recording head 1800, a magnetic circuit is provided at the top of the Figure, between the main magnetic pole 5 and the opposing magnetic pole 6. It should be noted that the head is assumed to be substantially electrically insulated at the top of the Figure. In a magnetic circuit, the lines of magnetic force constitute a closed path, and it is not necessary that the circuit be formed solely of magnetic material. Also, a magnetic circuit may be formed by arrangement of an auxiliary magnetic pole, or the like, on the main magnetic pole 5 on a side facing the opposing magnetic pole 6. In this case, electrical insulation does not need to be provided between the main magnetic pole 5 and the auxiliary magnetic pole. In addition, it is assumed that the magnetic recording head 1800 is equipped with a coil and copper wire, etc., for exciting these magnetic circuits. An STO 1801, according to one embodiment, is formed between the main magnetic pole 5 and the opposing magnetic pole 6. The main magnetic pole 5 and the opposing magnetic pole 6 are provided with an electrode or some other suitable device for achieving electrical contact with an electrode, so that the STO drive current flows from the main magnetic pole 5 towards the opposing magnetic pole 6, or in the opposite direction. The material of the main magnetic pole 5 and the opposing magnetic pole 6 may be CoFe, a CoFe alloy of large saturation magnetization, or some other suitable material known in the art, with substantially no crystalline magnetic anisotropy. The recording medium 7 may comprise a substrate 19, a laminated film underlayer 20, and a recording layer 16 formed above the underlayer 20. The underlayer 20 may comprise a laminated structure having a 10 nm-Ru layer on a 30 nm-CoFe layer (or some other suitable material and thicknesses suitable for a laminated film known in the art). Also, the recording layer 16 may comprise a CoCrPt—SiOx layer having a total film thickness of about 15 nm (or some other suitable material and thicknesses suitable for a recording layer known in the art). The magnetic anisotropy magnetic field may have a strength of 15 kOe at 4 nm from the surface is provided, with the magnetic anisotropy increasing in stepwise fashion in the depth direction, and with the average magnetic anisotropy magnetic field being about 2.4 MA/m (30 kOe).

Adjacent to the main magnetic pole 5, there is formed an STO 1801 comprising in layered fashion: a non-magnetic spin dispersing material 8; a reference layer 3; a first non-magnetic spin conduction layer 4; a magnetic field generation layer (FGL) 1; a second non-magnetic spin conducting layer 14; a stabilizing layer (STL) 2; and a second non-magnetic spin dispersing material 9, toward the opposing magnetic pole 6. A pillar-like structure extending in the left-right direction in the Figure is shown, from the non-magnetic spin dispersing material 8 to the second non-magnetic spin dispersing material 9, having a rectangular shape with its longest direction along the media-facing surface, in cross-section.

Using this rectangular shape, shape anisotropy is produced in the track width direction, so, even when there is a leakage magnetic field component from the main magnetic pole 5 in the in-plane direction of the magnetic field generation layer 1, in-plane magnetization rotation occurs smoothly, and the main magnetic pole 5 and the magnetic field generation layer 1 may be made to approach each other. The length w of the side along the media-facing surface face of this rectangular structure is an important factor for determining the recording track width, and may be about 40 nm, or more or less in other approaches. In microwave-assisted recording, a recording medium of large magnetic anisotropy is used such that sufficient recording cannot be achieved unless the recording magnetic field from the main magnetic pole 5 and the high frequency magnetic field from the magnetic field generation layer 1 are aligned, so the width and thickness of the main magnetic pole 5 (length in the direction of head travel) may be large, so as to make it possible to apply a large recording magnetic field. In this embodiment, a recording magnetic field of about 0.9 MA/m may be obtained by adopting a width of about 60 nm, or more or less, and thickness of about 100 nm, or more or less.

As the RL 3, 1.5 nm-CoMnSi alloy (saturation magnetization 1.1 T) may be used, or some other suitable material in a suitable thickness as would be understood by one of skill in the art. The length from the end face of the main magnetic pole 5 to the end face of the opposing magnetic pole 6 may be in a range from about 35 nm to about 75 nm, such as about 49 nm, and a height of the magnetic field generation layer 1 may be in a range from about 25 nm to about 50 nm, such as about 38 nm.

Figure 19B:
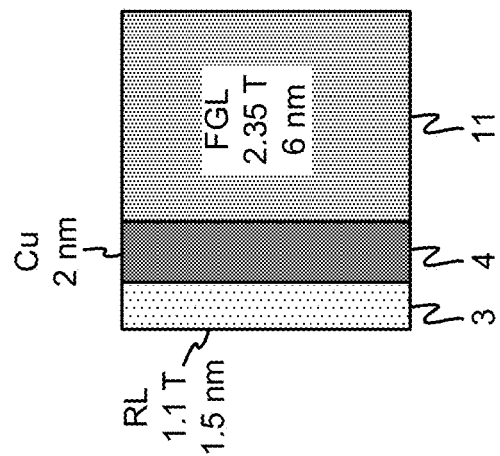
FIG. 19B is a diagram showing a layout of a conventional STO.
Figure 19A:
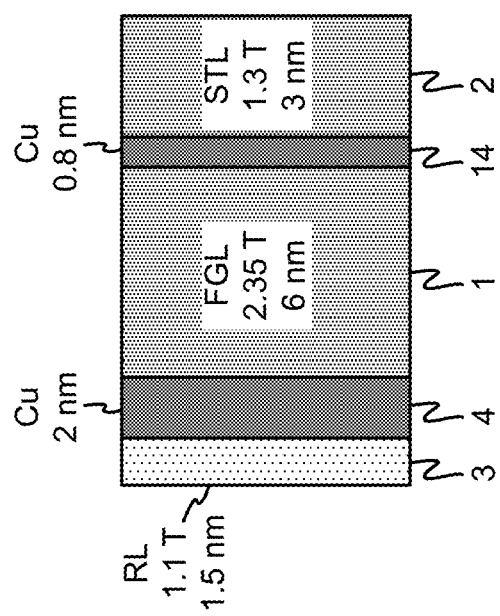
FIG. 19A is a diagram showing a layout of an STO according to one embodiment.

When the magnetic field applied to the STO in this embodiment was analyzed using 3D magnetic field analysis software, a value of about 0.8 MA/m (10 kOe) was obtained. As the magnetic field generation layer 1, a CoFe alloy (saturation magnetization of 2.35 T) may be used, or some other suitable material known in the art, having a large saturation magnetization. A thickness of the FGL 1 may be in a range from about 2 nm to about 10 nm, such as about 6 nm, with scarcely any crystal magnetic anisotropy. For the stabilizing layer (STL) 2, a (Ni/Co)n alloy (saturation magnetization of about 1.1 T) may be used, or some other suitable material known in the art, with a thickness in a range from about 0.5 nm to about 6 nm, such as about 3 nm and a crystal magnetic anisotropy of about 7 kOe may be used (as shown in FIG. 19A). Also, for comparison, an STO of the conventional type was concurrently manufactured (as shown in FIG. 19B), in which no second non-magnetic spin conduction layer or stabilizing layer (STL) were formed, using a magnetic field generation layer 1 comprising a CoFe alloy (saturation magnetization of about 2.35 T) and a thickness of about 6 nm.

In the magnetic field generation layer, the magnetization rotates at high speed in the plane along the layer; leakage magnetic field from the media-facing surface and from the magnetic pole, appearing at the side face, acts as a high-frequency magnetic field. When a material of large saturation magnetization having negative perpendicular magnetic anisotropy, such as a (CoFe)n multi-layer film, is employed as the magnetic field generation layer 1, the in-plane rotation of the magnetization stabilized, and a more intense high-frequency magnetic field is thereby obtained, in this approach.

Referring again to FIG. 18, in the STO 1801 according to this embodiment, the STO drive current (DC) flows from the magnetic field generation layer 1 towards the RL 3, in order to obtain AF mode spin torque oscillation.

When flux flows in from the main magnetic pole 5, the direction of rotation of the magnetic field generation layer magnetization is clockwise as seen from the side of the main magnetic pole 5, so a high-frequency magnetic field may be applied which is in the same direction of rotation as the direction of preceding movement of the magnetization of a recording medium, where magnetization inversion is desired by positioning between the main magnetic pole 5 and the magnetic field generation layer 1. When the magnetic flux flows towards the main magnetic pole 5, the direction of rotation of the magnetic field generation layer magnetization is anticlockwise, as seen from the main magnetic pole 5; thus, high-frequency magnetic flux may be applied which is in the same direction of rotation as the preceding movement of the magnetization of a recording medium, in which magnetization inversion is desired. Consequently, a beneficial effect where the rotating high-frequency magnetic field that is generated from the magnetic field generation layer 1 assists production of magnetization inversion by the main magnetic pole 5 is obtained, independently of the polarity of the main magnetic pole 5. This beneficial effect is not obtained with conventional high-frequency magnetic generators, in which the spin torque direction is not changed by the polarity of the main magnetic pole 5.

The spin torque action increases as the STO drive current (electron current) increases, and becomes large when Co, which is of high polarizability, is inserted to an extent of about 0.5 nm, or more or less, between the non-magnetic spin conduction layer and the adjacent ferromagnetic layer. For the first non-magnetic spin conduction layer 4, 2 nm-Cu may be used, or some other suitable conductive material in some other suitable thickness known in the art. For the second non-magnetic spin conduction layer 14, 0.8 nm-Cu may be used, or some other suitable conductive material in some other suitable thickness known in the art. For the non-magnetic spin dispersing material 8 and 9, 3 nm-Ru may be used, or some other suitable material in some other suitable thickness known in the art.

Figure 20:
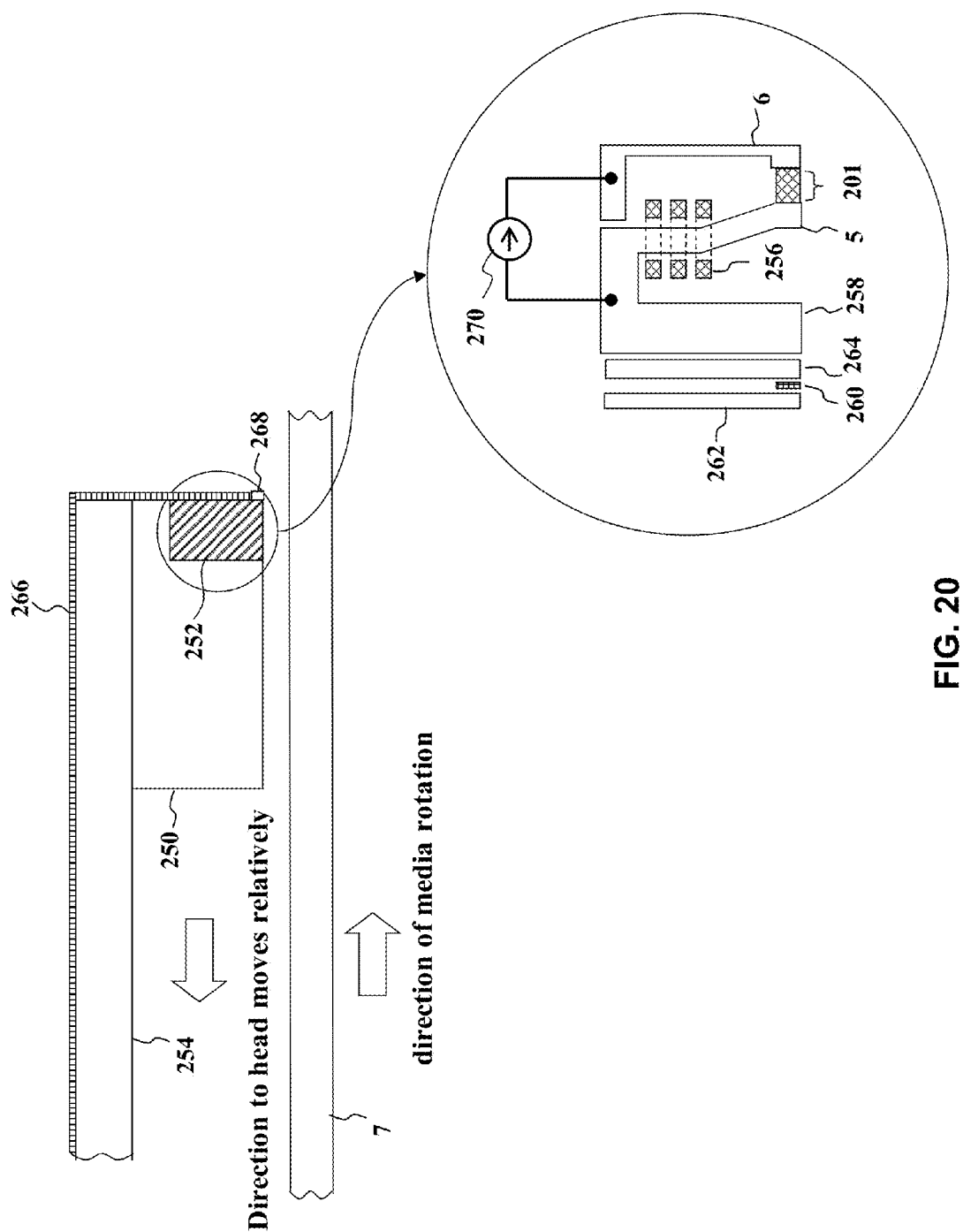
FIG. 20 is a cross-sectional view to a larger scale, showing a slider and a recording/reproduction unit which is mounted therein in one embodiment.

As shown in FIG. 20, a magnetic head slider 250 was tested in which a recording/reproduction unit 252 was mounted, incorporating an STO 201 according to one embodiment, on a suspension 254. The recording/reproduction performance on the magnetic medium 7 was investigated, using a spin stand. The recording/reproduction unit 252 comprised a recording head unit and a reproduction head unit. As shown in the detail view, the recording head comprises a coil 256 that excites the main magnetic pole, and an STO 201 that is arranged between the main magnetic pole 5 and an opposing magnetic pole 6, and an auxiliary magnetic pole 258. The reproduction head unit comprises a reproduction sensor 260 that is arranged between a lower shield 262 and an upper shield 264. In some cases, the auxiliary magnetic pole 258 and the upper shield 264 may be combined. The drive current of the various constituent elements of the recording/reproduction unit 252 is supplied by a wiring 266 and is supplied to the various constituent elements by terminals 268. In the detail view, the power source 270 for supplying current to the STO 201 is shown diagrammatically, but, in fact, the power source 270 may be arranged outside the slider 250 and the STO drive current produced by the power source 270 may be supplied to the STO 201 through the wiring 266.

Magnetic recording was performed using a head medium relative speed of 20 m/s, a magnetic spacing of 7 nm, and track pitch of 50 nm. This recording was then reproduced by a GMR head having a shield gap of 15 nm. When a signal of 1300 kFCI was recorded at 512 MHz without passing a STO drive current, the signal/noise ratio (SNR) was 9.0 dB, whether an STL was included in the head or not. The effect of microwave assistance was measured by passing current to the STO. The amount of increase of the SNR with and without STO drive current being supplied is defined as $\Delta$SNR, in terms of dB. If there is no STL, $\Delta$SNR is substantially 0 up to the point where the STO drive voltage exceeds 150 mV, and is saturated at about 200 mV, at 2.7 dB (SNR=11.7 dB); 340 mV was used in order to obtain 4.1 dB (SNR=13.1 dB). In contrast, in the case of the STO-mounted head equipped with an STL, $\Delta$SNR started to increase from an STO drive voltage of 65 mV, and 4.1 dB at 100 mV, 4.6 dB at 150 mV and 4.9 dB at 200 mV were obtained. From these results, it is evident that with an STO having an STL, a recording density exceeding 1 Tb per square inch may be achieved with an STO drive voltage of 100 mV. The frequency of the high-frequency magnetic field was 22.7 GHz in this case. Also, even when continuous writing operation was performed for 1000 hours at 100 mV, no change at all in the element resistance was found. When the STO drive current (DC) was reversed in direction, sufficient signal/noise was not obtained.

A further embodiment is described with reference to Tables 1-3. Tables 1-3 show the results of measuring the oscillation condition of the major parts of the STO, with the exception of the main magnetic pole 5, non-magnetic spin dispersing layers 8 and 9 and the opposing magnetic pole 6, in the trial-manufactured heads shown in FIG. 18. For the RLs 3, a 3.0 nm CoNi alloy film of saturation magnetization 1.1 T; a 3.0 nm CoMnGe alloy film of saturation magnetization 1.1 T; and a 1.5 nm CoMnGe alloy film of saturation magnetization 1.1 T were employed. The CoMnGe alloy is a type of Heusler alloy, of high spin polarizability, and is effective in lowering the STO drive current. In accordance with some embodiments, any of the RLs may comprise a Heusler alloy as a majority thereof (comprising 50% or greater of the material of the RL on an atomic or weight basis). FeCo of thickness 6 nm, of saturation magnetization 2.3 T, was employed for the FGL. The first non-magnetic spin conducting layer 4 was Cu of thickness 2 nm, while the second non-magnetic spin conduction layer 14 was Cu of thickness 0.8 nm. For the stabilizing layer (STL) 2, Ni (0.6 T), CoMnGe alloy (1.1 T), CoNi alloy (1.6 T), CoFe alloy (2.1 T) (hereinabove, Hk_STL=0, Group A), (Co/Pd) multilayer film (0.6 T), (Ni/Co) multilayer film (1.1 T), (Co/Ni) multilayer film (1.6 T) (hereinabove, Hk_STL=7 kOe, Group B) were respectively formed, with thicknesses in the range of about 1 nm to about 6 nm. Also, for comparison, an STO with no stabilizing layer was manufactured for testing.

Measurement was conducted by applying a magnetic field of 11 kOe from outside, inclined at an angle of 10° from the film surface, and the STO drive voltage was varied from 0 to 250 mV over 30 sec. The oscillation frequency was associated with the STO drive voltage, finding the peaks by Fourier transformation of the magnetoresistance. When the STO drive voltage was low, as shown in FIG. 9A, the oscillation frequencies of the FGL-1 and the RL did not coincide, so the magnetoresistance changed in irregular fashion, so that well-defined peaks were not obtained even by performing Fourier transformation. When the STO drive voltage exceeds the critical voltage Vc (critical current Jc in FIG. 9A), the magnetization rotations of the FGL-1 and the RL are synchronized, so that measurement of the oscillation frequency is achievable, taking the difference of relative angle of the external magnetic field and each layer as the magnetoresistance output. It should be noted that if the STO is driven below Vc, the oscillation frequencies of the FGL-1 and the RL do not coincide, so the rotation of the FGL-1 is disrupted by the rotation of the RL: this is therefore undesirable for assisted recording. Tables 1-3 show the critical voltage Vc and the frequency when V=100 mV (in the case of Vc when Vc>100 mV).

Table 1, below, shows the oscillation characteristic when a CoNi alloy film of saturation magnetization 1.1 T and thickness 3.0 nm is employed for the RL.

TABLE 1

| | | Group A | | |
|---|---|---|---|---|
| | | | STL | |
| | | (Co/Pd) | (Ni/Co) | (Co/Ni) |
| Vc(mV) | | | | |
| tSTL (nm) | 6 | 55 | 55 | 70 |
| | 3 | 75 | 85 | 120 |
| | 2 | 105 | 100 | 190 |
| | 1 | — | 205 | — |
| f (GHz) | | | | |
| tSTL (nm) | 6 | 28.9 | 26.3 | 20.5 |
| | 3 | 20.9 | 16.4 | 16 |
| | 2 | 12 | 12 | 12.5 |
| | 1 | — | 15 | — |

| | | Group B | | |
|---|---|---|---|---|
| | | | STL | |
| | | Ni | CMG | CoNi | CoFe |
| Vc(mV) | | | | | |
| tSTL (nm) | 6 | 105 | 115 | — | — |
| | 3 | 175 | 250 | — | — |
| | 2 | 250 | — | — | — |
| | 1 | — | — | — | — |
| f (GHz) | | | | | |
| tSTL (nm) | 6 | 13.1 | 12.5 | — | — |
| | 3 | 13 | 13 | — | — |
| | 2 | 13 | — | — | — |
| | 1 | — | — | — | — |

In the case where there is no stabilizing layer (STL), even for an STO drive voltage of 250 mV, no well-defined peak was observed in the oscillation spectrum. When Group A (Hk_STL=0) was employed for the stabilizing layer (STL), it was possible to observe a critical voltage Vc with an Ni film and CMG film of at least 2 nm, albeit Vc could not be reduced below 100 mV. The oscillation frequency at Jc was about 13 GHz. When Group B (HK_STL=7 kOe) was employed for the stabilizing layer (STL), Vc was considerably lowered, and Vc became less than 100 mV for the case of a (Co/Pd) multilayer film, a (Ni/Co) multilayer film of at least 2 nm, and a (Co/Ni) multilayer film of 6 nm. V=100 mV is a reference level of the STO drive voltage, such that the element resistance does not vary in continuous write operation for 1000 hours. This varies depending on manufacturing variability of the element resistance and element construction and the like, and so is a value that may be set in accordance with actual installation conditions, and therefore variation thereof is possible and may be accounted for in actual use.

In order to raise the oscillation frequency, at 28.9 GHz it is effective to employ a thick STL of low Bs comprising a (Co/Pd) multilayer film of thickness in a range from about 5 nm to about 8 nm, such as about 6 nm. However, in the case of a head in which the STL is too thick, it is necessary to increase the distance between the main magnetic pole and the opposing magnetic pole, so this reduces the write magnetic field, and, furthermore, reduces the magnetic field entering the STO, and so has the detriment that a large oscillation frequency cannot be achieved.

Table 2, below, shows the oscillation characteristic when a CoMnGe alloy film of saturation magnetization 1.1 T and thickness 3.0 nm is employed for the reference layer.

TABLE 2

| | | Group A | | | |
|---|---|---|---|---|---|
| | | | STL | | |
| | | Ni | CMG | CoNi | CoFe |
| Vc(mV) | | | | | |
| tSTL (nm) | 6 | 140 | — | — | — |
| | 3 | 140 | 160 | 195 | — |
| | 2 | 160 | 165 | 190 | 210 |
| | 1 | 175 | 175 | 190 | 210 |
| f (GHz) | | | | | |
| tSTL (nm) | 6 | 23 | — | — | — |
| | 3 | 18 | 20 | 20 | 31.4 |
| | 2 | 19 | 19 | 20 | 20 |
| | 1 | 19 | 2 | 20 | 20 |

| | | Group B | | |
|---|---|---|---|---|
| | | | STL | |
| | | (Co/Pd) | (Ni/Co) | (Co/Ni) |
| Vc(mV) | | | | |
| tSTL (nm) | 6 | 70 | 65 | 65 |
| | 3 | 90 | 105 | 140 |
| | 2 | 110 | 115 | 170 |
| | 1 | 155 | 140 | 160 |
| f (GHz) | | | | |
| tSTL (nm) | 6 | 28.9 | 26.5 | 19.9 |
| | 3 | 21.6 | 22 | 20 |
| | 2 | 20 | 19.5 | 20 |
| | 1 | 21 | 20 | 20.5 |

CoMnGe alloy has a high spin polarizability and so is effective in lowering the STO drive current. When no stabilizing layer (STL) was provided, Vc=240 mV, and the oscillation frequency was then 11.6 GHz. Stable oscillation cannot be obtained merely by increasing the spin polarizability of the reference layer. When Group A (HK_STL=0) was employed for the stabilizing layer (STL), a critical voltage Vc could be observed even with an STL film thickness of 1 nm, albeit, as in Table 1's Group A, Vc could not be made smaller than 100 mV. The oscillation frequency at Vc is about 50% larger, at about 20 GHz, compared with Table 1's Group A. Also, when the product of the saturation magnetization (Bs_STL) and the film thickness (t_STL) of the STL exceeds 6 nmT, the spin torque acting on the STL becomes small, with the result that stability is lowered and the layer no longer functions as a stabilizing layer, Bs_STL×t_STL<6 nmT.

The product of the saturation magnetization (Bs_STL) and the film thickness (t_STL) of the STL is desirably less than half the product of the saturation magnetization (Bs_FGL) and the film thickness (t_FGL) of the FGL. Referring again to Table 2, even when Group B (Hk_STL=7 kOe) is employed for the stabilizing layer (STL), Vc was considerably lowered, and it became possible to observe a critical voltage Vc even with an STL film thickness of 1 nm. When Vc is 100 mV or less, although substantially the same as in the case of Table 1's Group B, referring again to Table 2, the oscillation frequency at Vc is about 20 GHz, i.e., it is about 50% larger than in the case of Table 1's Group B. It is therefore believed that, regarding the oscillation frequency at Vc, it is effective to raise the spin polarizability of the reference layer. Also, in order to lower Vc, it is effective to make the ratio of the film thickness (t_STL) with respect to the saturation magnetization (Bs_STL) of the STL exceed 2 nm/T, t_STL/Bs_STL>2 nm/T.

From the two expressions, it is effective to employ a film thickness of the STL in the range determined by the expression: 2×Bs_STL<t_STL<6/Bs_STL. When Bs_STL=0.5 T, this thickness will be about 1 to 12 nm; when Bs_STL=1.0 T, this thickness will be about 2 to 6 nm; and when Bs_STL=1.5 T, this thickness will be about 3 to 4 nm.

Table 3, below, shows the oscillation characteristic where a CoMnGe alloy film of saturation magnetization 1.1 T and of thickness 1.5 nm is employed for the reference layer.

TABLE 3

| | | Group A | | | |
|---|---|---|---|---|---|
| | | STL | | | |
| | | Ni | CMG | CoNi | CoFe |
| Vc(mV) | | | | | |
| tSTL (nm) | 6 | 85 | 105 | — | — |
| | 3 | 115 | 175 | — | — |
| | 2 | 160 | 190 | — | — |
| | 1 | 235 | 235 | — | — |
| f (GHz) | | | | | |
| tSTL (nm) | 6 | 15 | 17.5 | — | — |
| | 3 | 13 | 14 | — | — |
| | 2 | 15 | 15 | — | — |
| | 1 | 16 | 16 | — | — |
| | | Group B | | | |
| | | STL | | | |
| | | (Co/Pd) | (Ni/Co) | (Co/Ni) | |
| Vc(mV) | | | | | |
| tSTL (nm) | 6 | 50 | 55 | 50 | |
| | 3 | 60 | 65 | 105 | |

TABLE 3-continued

| | | | | | |
|---|---|---|---|---|---|
| | 2 | 85 | 80 | 130 | |
| | 1 | 165 | 135 | 170 | |
| f (GHz) | | | | | |
| tSTL (nm) | 6 | 29.4 | 26.8 | 22 | |
| | 3 | 22 | 22.7 | 13.4 | |
| | 2 | 18.6 | 18 | 14 | |
| | 1 | 16.1 | 15 | 15 | |

The CoMnGe alloy is thinner than in the case of Table 1, so its spin polarizability is lowered, but since the product of the saturation magnetization and the film thickness of the reference layer is lowered, this is effective to lower the STO drive current. When the stabilizing layer (STL) is absent, Vc=500 mV and the oscillation frequency is then 7.9 GHz. When Group A (Hk_STL=0) is employed for the stabilizing layer (STL), for a 6 nm Ni film, Vc is less than 100 mV. The oscillation frequency at Vc is about 15 GHz, i.e., 15% larger than in the case of Table 1's Group A.

Referring again to Table 3, when Group B (Hk_STL=7 kOe) is employed as the stabilizing layer (STL), excluding where the STL film thickness is 1 nm, the drop in Vc is the largest and, correspondingly, the oscillation frequency at V=100 mV is at a maximum. The effective STL film thickness substantially coincides with the expression: 2×Bs_STL<t_STL<6/Bs_STL.

Figure 10:
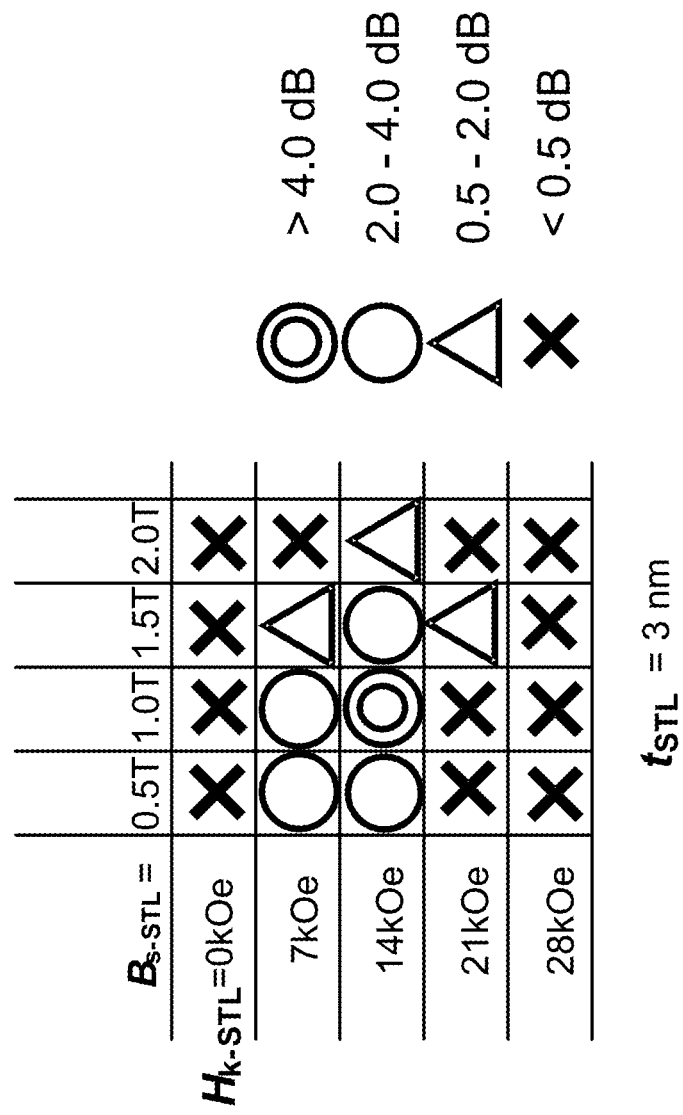
FIG. 10 shows calculated results of a SNR difference with a STO with a STL, while varying Hk and saturation magnetization of the STL, according to various embodiments.

As for determining an optimum value of Hk_STL, about 14 kOe is more preferable than 0 kOe to about 7 kOe, and is more preferable than about 21 kOe to about 28 kOe. FIG. 10 shows calculated results of the ΔSNR difference with a STO having a STL according to one embodiment, while varying Hk_STL and the saturation magnetization of the STL, Bs_STL. As can be seen, the greatest ΔSNR difference occurs with a Hk_STL of about 14 kOe and a Bs_STL of about 1.0 T. The calculations also take into account a 1 Tbit/in2 recording density.

As described above, it was found that a lowering of Jc(Vc) and an increase in the oscillation frequency may be achieved by: providing a stabilizing layer (STL) on the outside of the STO (i.e., on the opposite side of the STO from the RL, sandwiching the non-magnetic spin conduction layer of the FGL), in contrast to a conventional STO construction; conferring perpendicular magnetic anisotropy on the stabilizing layer; and raising the spin polarizability of the reference layer of the STO equipped with an STL. Consequently, the STO according to embodiments described herein may achieve prolongation of the element life and increased reliability.

Another embodiment is described with reference to FIG. 21. A characteristic feature of the main magnetic pole 5 of this embodiment is that it is inclined towards the side of the opposing magnetic pole 6, with reference to the media-facing surface. By inclining the main magnetic pole 5, it becomes possible to intensify the recording magnetic field and raise the recording magnetic field gradient. Also, since the gap magnetic field of the opposing magnetic pole 6 enters the lamination face of the STO 201 perpendicularly, it becomes possible to make the FGL approach more closely to the main magnetic pole 5. On the other hand, there was the drawback that the effective high-frequency magnetic field (anticlockwise component thereof) that is generated from the FGL is reduced. When an STO having an FGL-stack construction equipped with an STL according to embodiments presented herein is employed, the high-frequency magnetic field may be intensified, so excellent compatibility with a main magnetic pole 5 inclined as shown in FIG. 21 is achieved.

Figure 21:
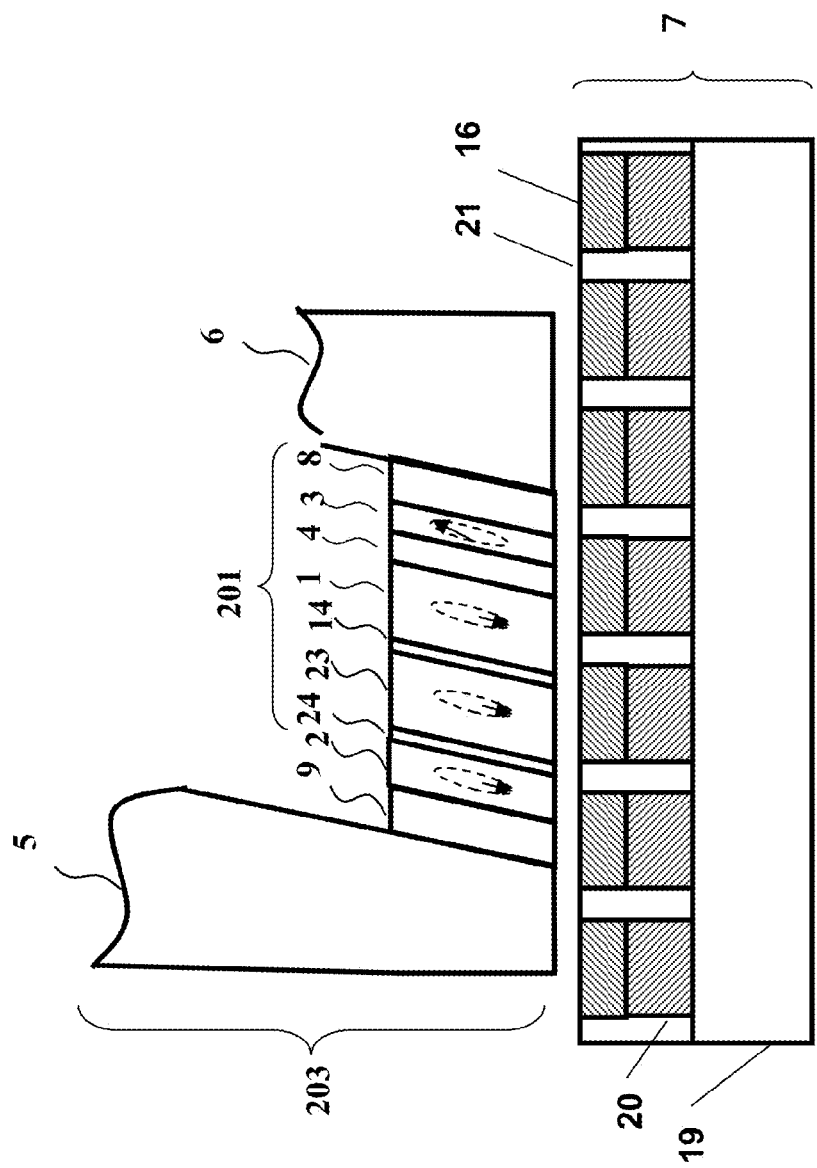
FIG. 21 is a diagrammatic cross-sectional view of a magnetic recording head according to one embodiment.

FIG. 21 is a cross-sectional view in which a magnetic recording head according to an embodiment is sectioned in a plane parallel with the direction of travel of the head (i.e., the track direction, which is the left and right direction in the Figure) and perpendicular to the recording medium surface (i.e., the vertical direction in the Figure). The Figure also shows the cross-section of the medium.

In regard to the recording head 203, a magnetic circuit is positioned at the top of the drawing, between the main magnetic pole 5 and the opposing magnetic pole 6. It should be noted that the head is assumed to be substantially electrically insulated at the top of the drawing. In a magnetic circuit, the lines of magnetic force comprise a closed path, and it is not necessary that the circuit should be formed solely of magnetic material. Also, a magnetic circuit may be formed by arrangement of an auxiliary magnetic pole or the like on the main magnetic pole 5 on side facing the opposing magnetic pole 6. In this case, electrical insulation does not need to be provided between the main magnetic pole 5 and the auxiliary magnetic pole. In addition, it is assumed that the magnetic recording head 203 is equipped with a coil and copper wire, etc., for exciting these magnetic circuits. An STO 201 according to one embodiment is formed between the main magnetic pole 5 and the opposing magnetic pole 6. The main magnetic pole 5 and the opposing magnetic pole 6 are provided with an electrode or a mechanism for achieving electrical contact with an electrode, so that the STO drive current flows from the main magnetic pole 5 towards the opposing magnetic pole 6, or in the opposite direction. The material of the main magnetic pole 5 and the opposing magnetic pole 6 may be a CoFe alloy of large saturation magnetization, with substantially no crystalline magnetic anisotropy. The recording medium 7 may comprise a substrate 19, a laminated film underlayer 20, and a recording layer 16 formed above the underlayer 20. The underlayer 20 may comprise a laminated structure having a 10 nm-Ru layer on a 30 nm-CoFe layer (or some other suitable material and thicknesses suitable for a laminated film known in the art). Also, the recording layer 16 may comprise a CoCrPt layer having a total film thickness of about 15 nm (or some other suitable material and thicknesses suitable for a recording layer known in the art). The recording layer 16 may have magnetic anisotropy magnetic field 15 kOe at 4 nm from the surface, with magnetic anisotropy that increases in stepwise fashion in the depth direction, the average magnetic anisotropy magnetic field being 2.8 MA/m(30 kOe), formed by etching with a pattern corresponding to 1.5 Tb per square inch (track pitch 46 nm, bit pitch 9 nm). SiOx may be embedded in the bit gaps 21.

Adjacent to the main magnetic pole 5, there is formed an STO 201 comprising in a layered fashion: a second non-magnetic spin dispersing material 9; a stabilizing layer (STL) 2; a third non-magnetic spin conducting layer 24; a second magnetic field generation layer 23 (FGL-2); a second non-magnetic spin conducting layer 14; a first magnetic field generation layer 1 (FGL-1); a first non-magnetic spin conducting layer 4; a reference layer 3; and a non-magnetic spin dispersing material 8; positioned toward the opposing magnetic pole 6.

A pillar-like structure is thereby positioned extending in the left-right direction in the Figure, from the non-magnetic spin dispersing material 9 to the second non-magnetic spin dispersing material 8, having a rectangular shape with its longest direction along the media-facing surface, in cross-section. Since the lamination faces are inclined, it should be noted that it is necessary to take care that the FGL is not easily magnetized in the height direction by the shape magnetic anisotropy. Magnetization in this direction when not oscillating would cause demagnetization of the recorded medium and is therefore undesirable. In the STO 201 of this embodiment, the reference layer 3 is between the opposing magnetic poles 6 and the first magnetic field generation layer 1, so, in order to obtain AF mode spin torque oscillation, it is useful to pass an STO drive current (DC) to the side of the opposing magnetic pole 6 from the side of the main magnetic pole 5.

As the reference layer 3, 3.0 nm-CoMnGe alloy (saturation magnetization 1.1 T) may be used, or some other suitable material of suitable thickness known in the art. The magnetic field applied to the STO according to the present embodiment may be about 11 kOe with a length of about 39 nm from the end face of the main magnetic pole 5 to the end face of the opposing magnetic pole 6, when analyzed using 3D magnetic field analysis software. For the first magnetic field generation layer (FGL-1) 1, a CoFe alloy (saturation magnetization 2.4 T) of large saturation magnetization, thickness 6 nm, and scarcely any crystalline magnetic anisotropy, may be employed, or some other suitable material of suitable thickness known in the art. For the second magnetic field generation layer (FGL-2) 23, a CoFe alloy of 5 or 6 nm thickness (saturation magnetization 2.4 T or 2.0 T) may be used, or some other suitable material of suitable thickness known in the art. For the stabilizing layer (STL) 2, Ni (saturation magnetization 0.6 T) of thickness 3 nm may be used, or some other suitable material of suitable thickness known in the art. In order to infer the optimum exchange interaction between the FGL-1 and the FGL-2 and between the FGL-2 and the STL, STOs may be manufactured in which the Cu thickness of the second non-magnetic spin conducting layer 14 and the third non-magnetic spin conducting layer 24 are respectively varied in a range of 0.5 to 0.8 nm and 0.6 to 2.0 nm, and incorporated in the recording head.

Figure 22A:
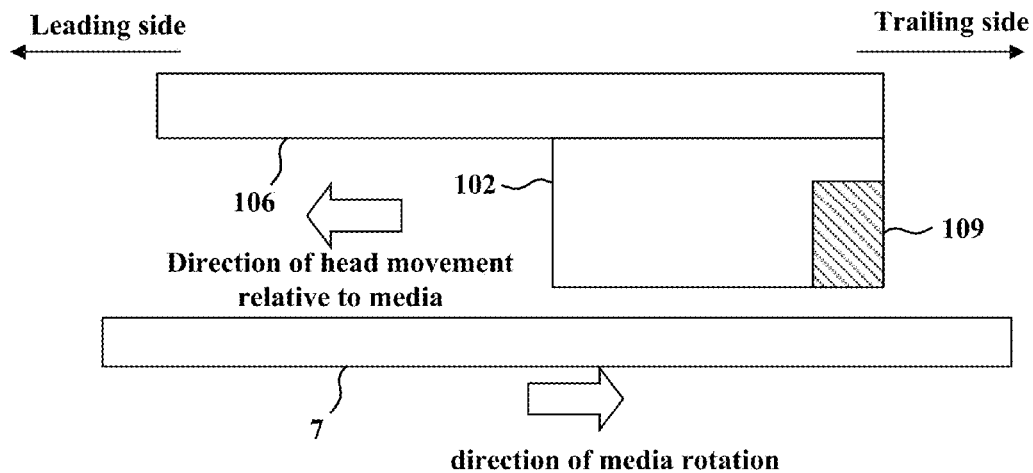
FIG. 22A is a view showing an example of the layout of a magnetic head slider and the magnetic head in one embodiment.
Figure 22B:
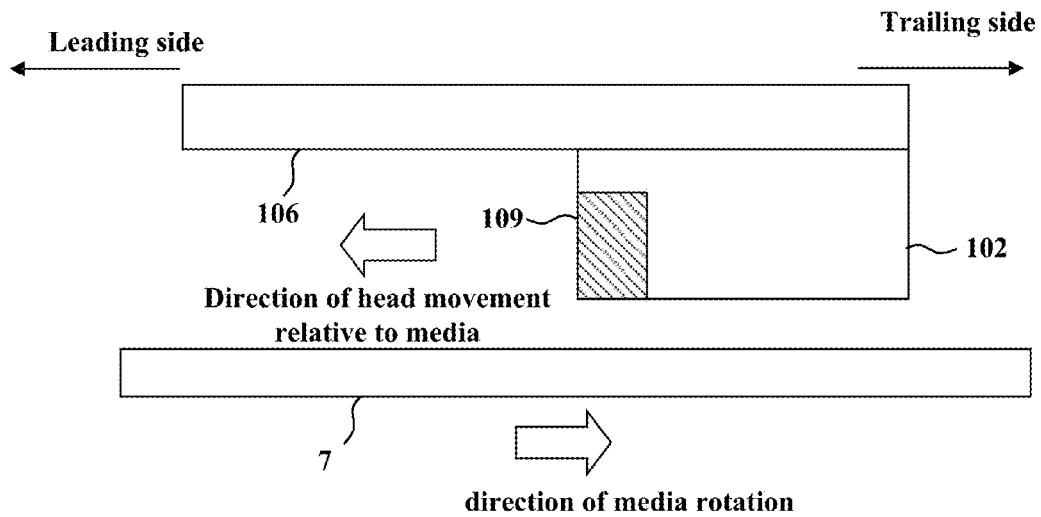
FIG. 22B is a view showing an example of the layout of a magnetic head slider and the magnetic head in another embodiment.

Also, for comparison, conventional STOs were concurrently manufactured, with an FGL-stack construction without an STL, of non-magnetic conductive material of thickness 3 nm, and in which no second non-magnetic spin conducting layer was formed between the FGL-1 and FGL-2, and with no stabilizing layer. The relationship of arrangement of the magnetic head travel direction and the recording medium is described, with reference to FIG. 22A and FIG. 22B. There are two modes of placement of the magnetic head on the magnetic head slider: one in which this is arranged on the trailing side, as shown in FIG. 22A, and another in which this is arranged on the leading side, as shown in FIG. 22B. It should be noted that the trailing side and the leading side are determined by the relative direction of movement of the magnetic head slider with respect to the recording medium: if the direction of rotation of the recording medium is opposite to the direction illustrated, FIG. 22A shows the situation in which the magnetic head is placed on the leading side, while FIG. 22B shows the situation in which the magnetic head is placed on the trailing side. Thus, although, in principle, if the recording medium were to be rotated in the opposite direction by inverting the polarity of the spindle motor, it would be possible to reverse the relationship of the trailing side and the leading side, because of the need to control the rotational speed precisely, it is impractical to change the polarity of the spindle motor.

Just as in the case of the embodiment of FIG. 18, magnetic recording was performed with a head-medium relative speed of 20 m/s, a magnetic spacing of 7 nm, and a track pitch of 50 nm, and, furthermore, this recording was then played back using a GMR head of shield gap 15 nm. When recording was performed of a signal of 1550 kFCI at 610 MHz, without passing STO drive current, the signal/noise ratio was 9.1 dB, irrespective of whether or not an FGL-stack construction was employed and irrespective of whether or not an STL was provided. Next, the microwave assistance effect was measured by passing current to the STO (STO drive voltage 150 mV). In the case where there was an FGL-stack construction, if there was no STL, even if current was supplied to the STO, ASNR was substantially 0 or a negative value. It is believed that the reason for this is that the STO either does not oscillate, or performs unstable oscillation, disrupting the recording magnetization. In the case of a conventional-type head in which the FGL-1 and FGL-2 were integrated, with no stabilizing layer, in the case where the total FGL thickness was 6 nm, ΔSNR=2.8 dB and, in the case where it was 11 to 12 nm, was 3.1 dB. By simple extrapolation from the ASNR values at 1 to 5 nm total FGL thickness, it would be expected that this value would exceed 5 dB at a thickness of 12 nm. It appears that the formation of magnetic domains in the thickness direction of the FGL suppresses increase in the intensity of the high-frequency magnetic field. Although the FGL-stack construction has the beneficial effect of preventing formation of such magnetic domains in the film thickness direction, it is useful that each FGL should rotate in the same phase in synchronization. If the product of the saturation magnetization and film thickness of the FGL-2 becomes too large, the spindle torque is insufficient, resulting in amplification of magnetization fluctuation between the FGLs, with the result that oscillation cannot be continued. By adding a stabilizing layer (STL) 2 according to the embodiments herein, the merit of the FGL-stack construction may be fully exploited.

Figure 23:
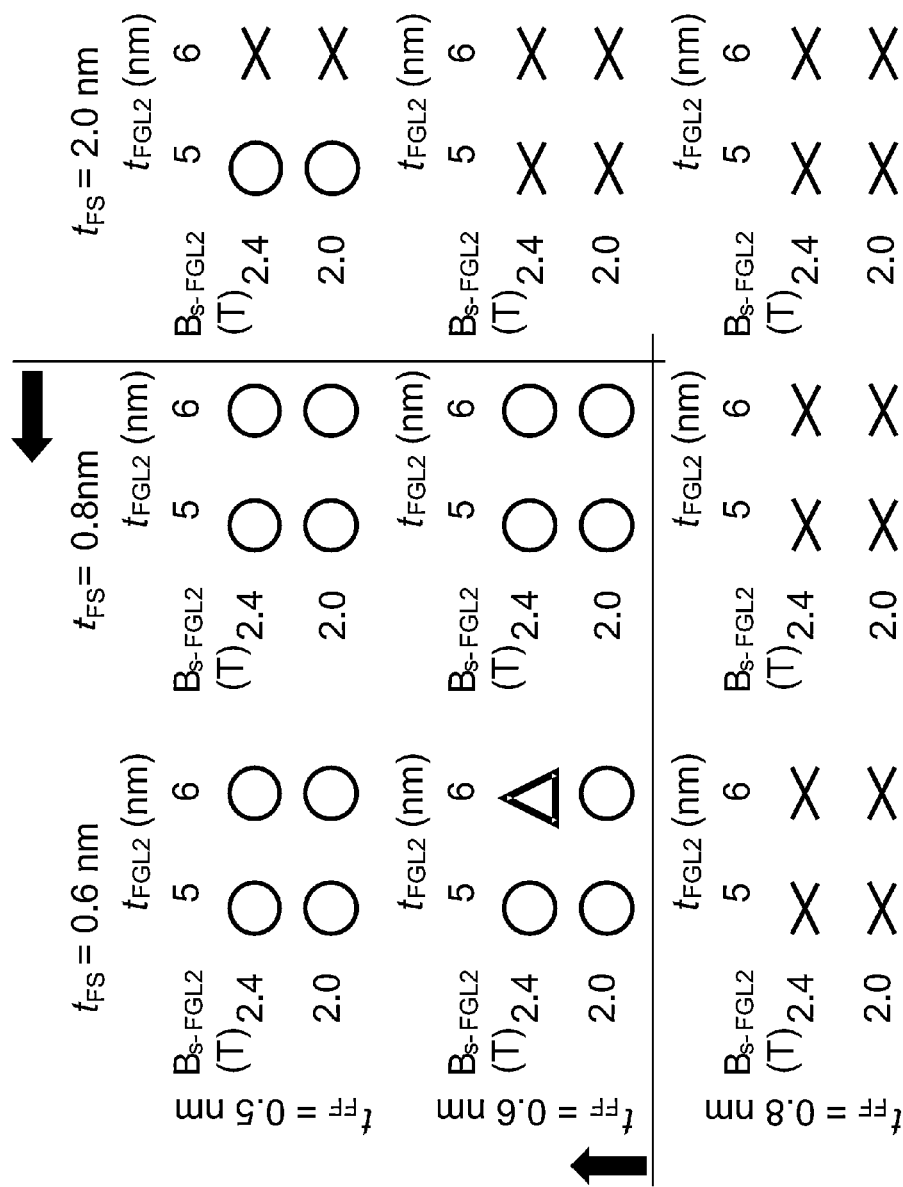
FIG. 23 is a view showing an effective range of a nonmagnetic spin conduction layer in various approaches.

FIG. 23 shows an investigation of the ASNR difference with a STO in which the FGL is integrated, while varying the saturation magnetization and film thickness of the second magnetic field generation layer (FGL-2), for a head in which the thickness of the second non-magnetic spin conducting layer (t_FF) and the thickness (t_FS) of the third non-magnetic spin conducting layer were varied. Cases in which the ASNR difference was substantially zero or negative were indicated by X; cases in which this difference exceeded 1 dB and SNR=13.1 dB was obtained were indicated by A; and cases in which this difference exceeded 2 dB were indicated by O.

From the Figure, it appears that, when the thickness (t_FF) of the second non-magnetic spin conducting layer is greater than about 0.6 nm, in-phase synchronized rotation cannot be obtained. Also, preferably the thickness (t_FS) of the third non-magnetic spin conducting layer may be less than about 0.8 nm. From the laminated structure of the CoFe alloy, it is inferred that the exchange interactions acting in the case of Cu thicknesses of 0.6 nm and 0.8 nm are respectively 2 erg/cm2 and 1 erg/cm2. It also appears desirable to intensify coupling between the FGLs.

Furthermore, it is preferable to make the coupling between the FGLs stronger on the reference layer side when the FGLs comprise three or more layers. From the above, it appears that, in an STO having an FGL-stack construction equipped with an STL according to embodiments herein, the high-frequency magnetic field is intensified, so recording densities exceeding 1.2 Tb per square inch may be achieved. The frequency of the high-frequency magnetic field is then 18.0 GHz. Furthermore, with an STO having an FGL-stack construction equipped with an STL employing, as the reference layer, 1.5 nm-CoMnGe alloy (saturation magnetization 1.1 T) and, as the stabilizing layer (STL), (Co/Ni) multilayer film of thickness 3 nm (saturation magnetization 1.1 T and magnetic anisotropy 7 kOe), a fully sufficient SNR and overwrite performance were achieved in recording and reproduction with a recording density exceeding 1.5 Tb per square inch. Also, even when subjected to continuous write operation for 1000 hours at 100 mV, no change at all in the element resistance was found.

Figure 24B:
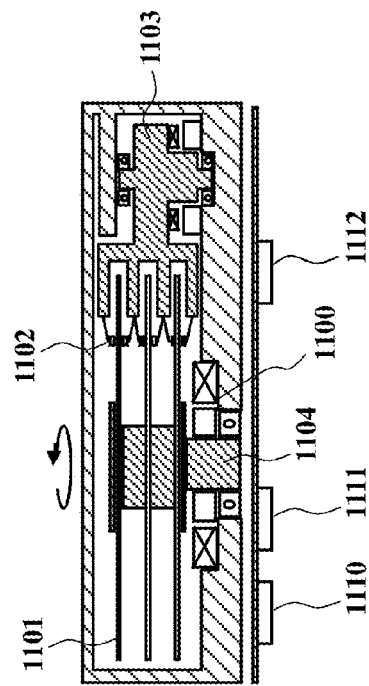
FIG. 24B is a cross-sectional view along the line A-A' of FIG. 24A in one embodiment.
Figure 24A:
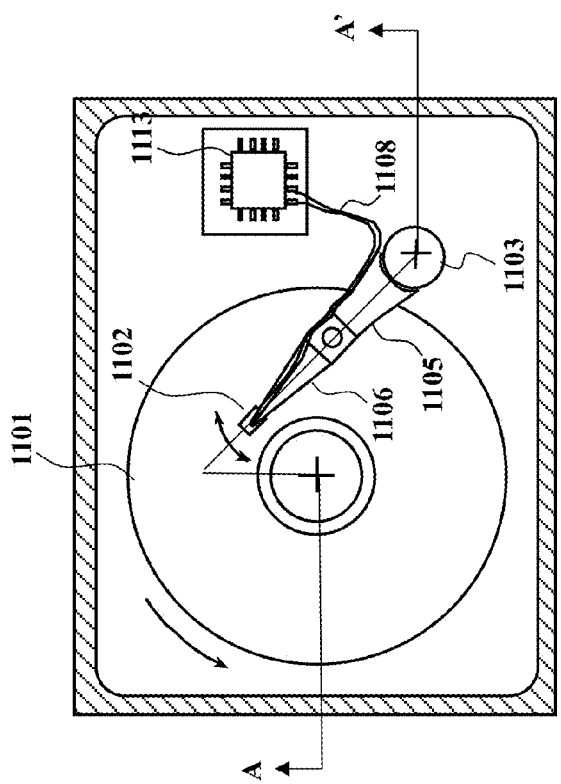
FIG. 24A is a plan diagram of a magnetic recording device in one embodiment.

A further embodiment is described with reference to FIGS. 24A-24B. FIG. 24A and FIG. 24B show the overall construction of a magnetic recording device according to one embodiment, with FIG. 24A being a plan view and FIG. 24B being a cross-sectional view along A-A' thereof. The recording medium 1101 is fixed to a rotary shaft bearing 1104, and is rotated by a motor 1100. FIG. 24B shows an example in which three magnetic discs and six magnetic heads are provided; however, there could be one or more magnetic discs and one or more magnetic heads. The recording medium 1101 is disc-shaped and is formed with recording layers on both faces thereof. The slider 1102 moves substantially in the radial direction over the surface of the rotating recording medium and is provided with a recording/reproduction unit at its tip. The recording/reproduction unit, an STO, and a main magnetic pole are provided in the recording unit as described in more detail previously.

A suspension 1106 is supported on a rotary actuator 1103 using an arm 1105. The suspension 1106 has the function of trying to press the slider 1102 onto the recording medium 1101 with a prescribed load, or to pull it away therefrom. Current for driving the various constituent elements of the magnetic head is supplied from an IC amplifier 1113 through wiring 1108. The processing of the recording signal that is supplied to the recording head unit and/or the reproduction signal that is detected from the reproduction head unit is executed by a channel IC 1112 for reading/writing, shown in FIG. 24B. Also, control operation of the magnetic recording device as a whole is implemented by a processor 1110 executing a disc control program stored in memory 1111. Consequently, in the case of this embodiment, the processor 1110 and the memory 1111 comprise a so-called disk controller.

Figure 25:
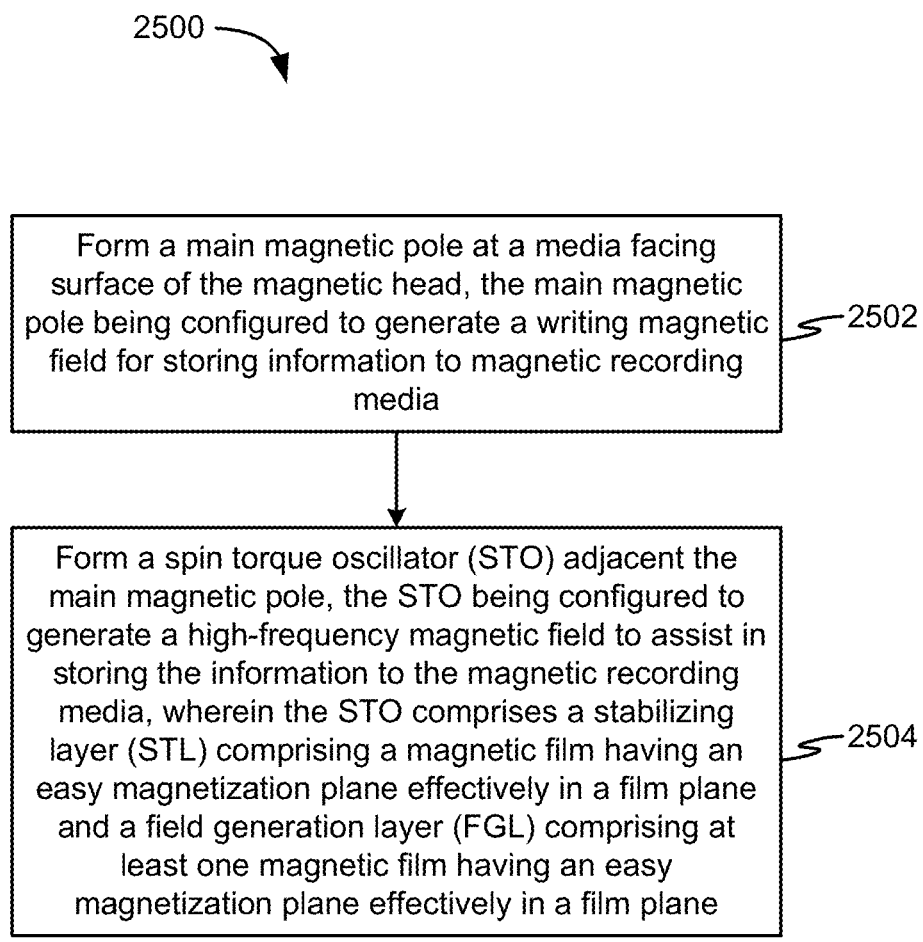
FIG. 25 shows a flowchart of a method according to one embodiment.

In FIG. 25, a method 2500 for forming a MAMR head is shown according to one embodiment. The method 2500 may be implemented in any desired environment, including but not limited to those depicted in FIGS. 1-24B, among others.

In operation 2502, a main magnetic pole is formed at a media facing surface of the magnetic head. The main magnetic pole is configured to generate a writing magnetic field for storing information to magnetic recording media, and may comprise any suitable material known in the art, and may have a thickness as would be suitable as would be known by one of skill in the art.

In operation 2504, a STO is formed adjacent the main magnetic pole using any formation technique known in the art, such as sputtering, plating, chemical vapor deposition, etc. The STO is configured to generate a high-frequency magnetic field to assist in storing the information to the magnetic recording media. The STO comprises a STL of a type described herein that comprises a magnetic film having an easy magnetization plane effectively in a film plane thereof, and a FGL comprising at least one magnetic film having an easy magnetization plane effectively in a film plane.

In various embodiments, a magnetization of the STL may be capable of in-plane rotation, a magnetization of the FGL may be capable of in-plane rotation, and/or a product of a saturation magnetization of the STL multiplied by a thickness of the STL may be less than half a product of a magnetization of the FGL multiplied by a thickness of the FGL.

In a further embodiment, forming the STO may comprise forming a reference layer having a magnetization that is capable of free in-plane rotation, forming a first non-magnetic spin conducting layer adjacent the reference layer, forming the FGL adjacent the first non-magnetic spin conducting layer, forming a second non-magnetic spin conducting layer adjacent the FGL, and forming the STL adjacent the second non-magnetic spin conducting layer such that the STL is positioned on a side of the STO opposite the reference layer.

The spin conducting layers may comprise Cu, AgSn, AgZn, Al-based alloys, Heusler alloys such as CoGeMn, and/or any other suitable material for transferring spin torque as would be known in the art.

The STL may have a maximum thickness, in some embodiments, of about 10 nm, and much thinner layers may be used, such as in a range from about 1.5 nm to about 5 nm, up to about 6 nm when using CoFe for the FGL, and up to about 7-8 nm when using other materials for the FGL. The maximum width of the STO may be about 20-25 nm in some embodiments.

In another embodiment, a product of a saturation magnetization of the reference layer multiplied by a thickness of the reference layer is less than half a product of a magnetization of the FGL multiplied by a thickness of the FGL.

In alternate embodiments, the STL may be configured to pass current to the reference layer during operation thereof, or the reference layer may be configured to pass current to the STL during operation thereof.

In one approach, the reference layer may comprise a Heusler alloy as a majority thereof, e.g., 50% or greater in atomic or weight percentage.

In another embodiment, a ratio of the thickness of the STL to the saturation magnetization of the STL may be greater than about 2 nm/T. In yet another embodiment, the STL may have perpendicular magnetic anisotropy as described herein in more detail.

Additionally, forming the FGL may include forming a laminated stack that comprises two or more free rotation layers, each of the two or more free rotation layers being separated from one another by magnetic spin conduction layers. In this embodiment, each magnetic spin conduction layer may have a thickness of no greater than about 1 nm.

It should be noted that methodology presented herein for at least some of the various embodiments may be implemented, in whole or in part, in computer hardware, software, by hand, using specialty equipment, etc., and combinations thereof.

Moreover, any of the structures and/or steps may be implemented using known materials and/or techniques, as would become apparent to one skilled in the art upon reading the present specification.

The inventive concepts disclosed herein have been presented by way of example to illustrate the myriad features thereof in a plurality of illustrative scenarios, embodiments, and/or implementations. It should be appreciated that the concepts generally disclosed are to be considered as modular, and may be implemented in any combination, permutation, or synthesis thereof. In addition, any modification, alteration, or equivalent of the presently disclosed features, functions, and concepts that would be appreciated by a person having ordinary skill in the art upon reading the instant descriptions should also be considered within the scope of this disclosure.

While various embodiments have been described above, it should be understood that they have been presented by way of example only, and not limitation. Thus, the breadth and scope of an embodiment of the present invention should not be limited by any of the above-described exemplary embodiments, but should be defined only in accordance with the following claims and their equivalents.

What is claimed is:

1. A device, comprising:
a main magnetic pole positioned at a media facing surface of the device; and
a spin torque oscillator (STO) positioned adjacent the main magnetic pole, the STO being configured to generate a high-frequency magnetic field to assist in storing the information to the magnetic recording media,
wherein the STO comprises:
a field generation layer (FGL) comprising at least one magnetic film having an easy magnetization plane effectively in a film plane, wherein a magnetization of the FGL is capable of in-plane rotation;
a reference layer having a magnetization that is capable of free in-plane rotation; and
a stabilizing layer (STL) positioned on a side of the FGL opposite the reference layer, the STL comprising a magnetic film having an easy magnetization plane effectively in a film plane, wherein a magnetization of the STL is capable of in-plane rotation, and
wherein a product of a saturation magnetization of the STL multiplied by a thickness of the STL is less than half a product of a magnetization of the FGL multiplied by a thickness of the FGL.

2. The device as recited in claim 1, further comprising a first non-magnetic spin conducting layer positioned between the reference layer and the FGL.

3. The device as recited in claim 1, further comprising a second non-magnetic spin conducting layer positioned between the STL and the FGL.

4. The device as recited in claim 1, wherein a product of a saturation magnetization of the reference layer multiplied by a thickness of the reference layer is less than half a product of a magnetization of the FGL multiplied by a thickness of the FGL.

5. The device as recited in claim 1, wherein current passes from the STL to the reference layer during operation.

6. The device as recited in claim 1, wherein current passes from the reference layer to the STL during operation.

7. The device as recited in claim 1, wherein the STL has perpendicular magnetic anisotropy.

8. The device as recited in claim 7, wherein a ratio of the thickness of the STL to the saturation magnetization of the STL is greater than about 2 nm/T.

9. The device as recited in claim 1, wherein the reference layer comprises a Heusler alloy as a majority thereof.

10. The device as recited in claim 1, wherein the FGL comprises a laminated stack that comprises two or more free rotation layers, each of the two or more free rotation layers being separated from one another by magnetic spin conduction layers.

11. The device as recited in claim 10, wherein each magnetic spin conduction layer has a thickness of no greater than about 1 nm.

12. The device as recited in claim 1, further comprising:
a magnetic medium;
a drive mechanism for passing the magnetic medium over the main magnetic pole; and
a controller electrically for controlling operation of the main magnetic pole.

13. A device, comprising:
a main magnetic pole positioned at a media facing surface of the device; and
a spin torque oscillator (STO) positioned adjacent the main magnetic pole, wherein the STO comprises:
a field generation layer (FGL) comprising at least one magnetic film having an easy magnetization plane effectively in a film plane, wherein a magnetization of the FGL is capable of in-plane rotation;
a reference layer having a magnetization that is capable of free in-plane rotation; and
a stabilizing layer (STL) positioned on a side of the FGL opposite the reference layer, the STL comprising a magnetic film having an easy magnetization plane effectively in a film plane, wherein a magnetization of the STL is capable of in-plane rotation.

14. The device as recited in claim 13, further comprising a first non-magnetic spin conducting layer positioned between the reference layer and the FGL.

15. The device as recited in claim 13, further comprising a second non-magnetic spin conducting layer positioned between the STL and the FGL.

16. The device as recited in claim 13, wherein a product of a saturation magnetization of the reference layer multiplied by a thickness of the reference layer is less than half a product of a magnetization of the FGL multiplied by a thickness of the FGL.

17. The device as recited in claim 13, wherein the STL has perpendicular magnetic anisotropy, and wherein a product of a saturation magnetization of the STL multiplied by a thickness of the STL is less than half a product of a magnetization of the FGL multiplied by a thickness of the FGL.

18. The device as recited in claim 13, wherein the FGL comprises a laminated stack that comprises two or more free rotation layers, each of the two or more free rotation layers being separated from one another by magnetic spin conduction layers, and wherein each magnetic spin conduction layer has a thickness of no greater than about 1 nm.

19. The device as recited in claim 13, further comprising:
a magnetic medium;
a drive mechanism for passing the magnetic medium over the main magnetic pole; and
a controller electrically for controlling operation of the main magnetic pole.

20. A device, comprising:
a main magnetic pole positioned at a media facing surface of the device, the main magnetic pole being configured to generate a writing magnetic field for storing information to magnetic recording media; and
a spin torque oscillator (STO) positioned adjacent the main magnetic pole, the STO being configured to generate a high-frequency magnetic field to assist in storing the information to the magnetic recording media,
wherein the STO comprises:
a reference layer comprising a Heusler alloy as a majority thereof having a magnetization that is capable of free in-plane rotation;
a field generation layer (FGL) comprising at least one magnetic film having an easy magnetization plane effectively in a film plane, wherein a magnetization of the FGL is capable of in-plane rotation;
a first non-magnetic spin conducting layer positioned between the reference layer and the FGL;
a stabilizing layer (STL) positioned on a side of the FGL opposite the reference layer, the STL comprising a magnetic film having an easy magnetization plane effectively in a film plane, wherein a magnetization of the STL is capable of in-plane rotation; and
a second non-magnetic spin conducting layer positioned between the STL and the FGL,
wherein a product of a saturation magnetization of the STL multiplied by a thickness of the STL is less than half a product of a magnetization of the FGL multiplied by a thickness of the FGL,
wherein a product of a saturation magnetization of the reference layer multiplied by a thickness of the reference layer is less than half a product of the magnetization of the FGL multiplied by the thickness of the FGL, and
wherein a ratio of the thickness of the STL to the saturation magnetization of the STL is greater than about 2 nm/T.

* * * * *